United States Patent
Meruelo

(10) Patent No.: US 7,807,147 B2
(45) Date of Patent: *Oct. 5, 2010

(54) TUMOR THERAPY WITH HIGH AFFINITY LAMININ RECEPTOR-TARGETED VECTORS

(75) Inventor: Daniel Meruelo, Scarborough, NY (US)

(73) Assignee: New York University, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 11/928,564

(22) Filed: Oct. 30, 2007

(65) Prior Publication Data

US 2008/0125391 A1 May 29, 2008

Related U.S. Application Data

(63) Continuation of application No. 10/473,477, filed as application No. PCT/US02/09432 on Mar. 27, 2002, now Pat. No. 7,306,792.

(60) Provisional application No. 60/279,051, filed on Mar. 27, 2001, provisional application No. 60/311,373, filed on Aug. 10, 2001.

(51) Int. Cl.
  *A61K 48/00* (2006.01)
  *C12N 15/86* (2006.01)
(52) U.S. Cl. .................... 424/93.2; 424/93.6; 424/93.1; 435/456
(58) Field of Classification Search ................ None
  See application file for complete search history.

(56) References Cited

U.S. PATENT DOCUMENTS

| | | | |
|---|---|---|---|
| 5,091,309 A | 2/1992 | Schlesinger et al. | |
| 5,217,879 A | 6/1993 | Huang et al. | |
| 5,631,236 A * | 5/1997 | Woo et al. ................. | 514/44 |
| 5,739,026 A | 4/1998 | Garoff | |
| 5,789,245 A | 8/1998 | Dubensky, Jr. et al. | |
| 5,814,482 A * | 9/1998 | Dubensky et al. .......... | 435/69.3 |
| 5,843,723 A | 12/1998 | Dubensky, Jr. et al. | |
| 6,015,686 A | 1/2000 | Dubensky, Jr. et al. | |
| 6,015,694 A | 1/2000 | Dubensky, Jr. et al. | |
| 6,190,666 B1 | 2/2001 | Garoff et al. | |
| 6,224,879 B1 | 5/2001 | Sjoberg et al. | |
| 6,242,259 B1 | 6/2001 | Polo et al. | |
| 6,329,201 B1 | 12/2001 | Polo et al. | |
| 6,342,372 B1 | 1/2002 | Dubensky, Jr. et al. | |
| 6,376,236 B1 | 4/2002 | Dubensky, Jr. et al. | |
| 6,391,632 B1 | 5/2002 | Dubensky, Jr. et al. | |
| 6,426,196 B1 | 7/2002 | Dubensky, Jr. et al. | |
| 6,451,592 B1 | 9/2002 | Dubensky, Jr. et al. | |
| 6,458,560 B1 | 10/2002 | Dubensky, Jr. et al. | |
| 6,465,634 B1 | 10/2002 | Dubensky, Jr. et al. | |
| 6,566,093 B1 | 5/2003 | Liljestrom et al. | |
| 6,592,874 B2 | 7/2003 | Schlesinger et al. | |
| 6,692,750 B1 | 2/2004 | Sjoberg et al. | |
| 6,730,297 B1 | 5/2004 | Davidson et al. | |
| 6,770,283 B1 | 8/2004 | Garoff et al. | |

FOREIGN PATENT DOCUMENTS

| | | | |
|---|---|---|---|
| WO | WO-99/18226 | | 4/1999 |
| WO | WO 99/18799 | * | 4/1999 |
| WO | WO 99/44423 | * | 9/1999 |
| WO | WO 99/44423 A1 | | 9/1999 |
| WO | WO-00/62735 A | | 10/2000 |
| WO | 02/074920 | | 9/2002 |

OTHER PUBLICATIONS

Lundstrom (Gene Therapy 12: S92-S97, 2005).*
Tseng et al (Nature Biotechnology 22(1): 70-78, 2004).*
Karpf et al (Virology 240: 193-201, 1998).*
Tseng et al (Nature Biotechnology 22(1): 70-77, 2004).*
Frolov (J. Virol. 68(3): 1721-1727, 1994).*
Perri et al (J. Virol. 74(20):9802-9807, 2000).*
Miller et al. (FASEB J. 9: 190-199, 1995).*
Deonarain (Exp. Opin. Ther. Patents 8(1):53-69, 1998).*
Verma et al (Nature 389: 239-242, 1997).*
Crystal (Science 270: 404-410, 1995).*
Pouton et al (Adv. Drug Del. Rev. 46: 187-203, 2001).*
Read et al (Adv. Gen. 53:19-46, 2005).*
Higashikawa et al (Virology 280: 124-131, 2001).*
De Polo et al, J. Virol. 73 :6708-6714, 1999).*
Alemany et al (J. Gen. Virol 81: 2605-2609, 2000).*
Sung et al Mol. Ther. 3: 757-767, 2001).*
Unno et al (Clin. Cancer Res. 11(12): 4553-4560, 2005).*
Smerdou et al (J. Virol. 73: 1092-1098, 1999).*
Asselin-Paturel et al (Gene Therapy 5: 606-615, 1998).*
Zhang et al (Gene Therapy 4: 367-374, 1997).*
Leitner et al (Cancer Research 60: 51-55, 2000).*
Murphy et al (Gene Therapy 7: 1477-1482, 2000).*
Wang, et al. "High-Affinity Laminin Receptor Is a Receptor for Sindbis Virus in Mammalian Cells." Journal of Virology, vol. 66, No. 8, Aug. 1992, pp. 4992-5001.
Jan, et al. "Induction of Apoptosis by Sindbis Virus Occurs at Cell Entry and Does Not Require Virus Replication." Journal of Virology, vol. 73, No. 12, Dec. 1999, pp. 10296-10302.
Campo, et al. "Detection of Laminin Receptor mRNA in Human Cancer Cell Lines and Colorectal Tissues by In Situ Hybridization." American Journal of Pathology, vol. 141, No. 5, Nov. 1992, pp. 1073-1083.
Perri, Sylvia et al. "Replicon Vectors Derived from Sindbis Virus and Semliki Forest Virus That Establish Persistent Replication in Host Cells." Journal of Virology, Oct. 2000, pp. 9802-9807, vol. 74, No. 20.
Leitner, Wolfgang W. et al. "Enhancement of Tumor-specific Immune Response With Plasmid DNA Replicon Vectors." Cancer Research, Jan. 1, 2000, pp. 51-55.
Hariharan, Mangala J. et al. "DNA Immunization Against Herpes Simplex Virus: Enhanced Efficacy Using a Sindbis Virus-Based Vector." Journal of Virology, Feb. 1998, pp. 950-958, vol. 72, No. 2.

(Continued)

*Primary Examiner*—Richard Schnizer
(74) *Attorney, Agent, or Firm*—Fish & Richardson P.C.

(57) ABSTRACT

The present invention relates to methods and compositions for treating tumors using vectors that preferentially target tumor cells. In particular, the invention relates to alphavirus-based, preferably Sindbis virus-based, vectors and to non-alphavirus-based vectors, which have a preferential affinity for high affinity laminin receptors (HALR). These vectors are efficiently targeted to tumors and have the ability to cause tumor necrosis.

11 Claims, 1 Drawing Sheet

OTHER PUBLICATIONS

Gardner, Jason P. et al. "Infection of Human Dendritic Cells by a Sindbis Virus Replicon Vector Is Determined by a Single Amino Acid Substitution in the E2 Glycoprotein." Journal of Virology, Dec. 2000, pp. 11849-11857, vol. 74, No. 24.

Polo, John M. et al. "Stable Alphavirus Packaging Cell Lines for Sindbis Virus- and Semliki Forest Virus-Derived Vectors." Proc. Natl. Acad. Sci. USA, Apr. 1999, pp. 4598-4603, vol. 96.

Schlesigner, Sondra et al. "Alphavirus Vectors for Gene Expression and Vaccines." Current Opinion in Biotechnology, 1999, pp. 434-439.

Dubensky, Thomas W., Jr. et al. "Sindbis Virus DNA-Based Expression Vectors: Utility for In Vitro and In Vivo Gene Transfer." Journal of Virology, Jan. 1996, pp. 508-519, vol. 70, No. 1.

Xiong, Cheng et al. "Sindbis Virus: An Efficient, Broad Host Range Vector for Gene Expression in Animal Cells." Science, Mar. 3, 1989, pp. 1188-1191, vol. 243.

Levis, Robin et al. "Engineered Defective Interfering RNAs of Sindbis Virus Express Bacterial Chloramphenicol Acetyltransferase in Avian Cells." Proc. Natl. Acad. Sci. USA, Jul. 1987, pp. 4811-4815, vol. 84.

Ying H. et al., "Cancer Therapy Using a Self-Replicating RNA Vaccine", Nature Medicine, Jul. 1999, pp. 823-827, vol. 5, No. 7, Nature Publishing Group, New York, USA.

Schlesinger S. et al., "Alphavirus Vectors for Gene Expression and Vaccines", Current Opinion in Biotechnology, Oct. 1999, pp. 434-439, vol. 10, No. 5, London, GB.

Klimp et al, "Activation of Peritoneal Cells Upon in Vivo Transfection with a Recombinant Alphavirus Expressing GM-CSF," *Gene Therapy*, Feb. 2000, vol. 8, No. 4, pp. 300-307.

Leitner et al, "Enhancement of Tumor-specific Immune Response with Plasmid DNA Replicon Vectors," *Cancer Research*, Jan. 1, 2000, vol. 60, No. 1, pp. 51-55.

Li et al, "Rescue of Sindbis Virus-Specific RNA Replication and Transcription by Using a Vaccinia Virus Recombinant," *Journal of Virology*, Dec. 1991, vol. 65, No. 12, pp. 6714-6723.

Cherig et al, "Cancer Immunotherapy Using Sindbis Virus Replicon Particles Encoding a VP22-Antigen Fusion," *Human Gene Therapy*, Mar. 1, 2002, vol. 13, No. 4, pp. 553-568.

Velders et al., "Eradication of Established Tumors by Vaccination with Venezuelan Equine Encephalitis Virus Replicon Particles Delivering Human Papillomavirus 16 E7 RNA," *Cancer Research*, Nov. 1, 2001, vol. 61, No. 21, pp. 7861-7867.

Wickham, Tom, 1997. "Short-order Sindbis vector targeting". Nature Biotechnology 15: 717.

Korokhov, et al., 2003. "Targeting of Adenovirus via Genetic Modification of the Viral Capsid Combined with a Protein Bridge". Journal of Virology 77(24): 12937-12940.

Henning, et al., 2002. "Genetic Modification of Adenovirus 5 Tropism by a Novel Class of Ligands Based on a Three-Helix Bundle Scaffold Derived from Staphylococcal Protein A". Human Gene Therapy 13: 1427-1439.

K. Imahori and T. Yamakawa, Editors, Dictionary of Biochemistry, 3rd edition, Tokyo Kagaku Doujin, p. 689.

Lin, et al, 1999. "Treatment of established tumors with a novel vaccine that enhances major histocompatibility class II presentation of tumor antigen." Cancer Research 56(1). Biosis abstract No. PREV199698682591.

Iijima, et al, 1999. "Cell-Specific Targeting of a Thymidine Kinase/ Ganciclovir Gene Therapy System Using a Recombinant Sindbis Virus Vector." Int. J. Cancer 80: 110-118.

* cited by examiner

SinRep/LacZ

DH-BB

US 7,807,147 B2

TUMOR THERAPY WITH HIGH AFFINITY LAMININ RECEPTOR-TARGETED VECTORS

This application is a continuation of Ser. No. 10/473,477, filed Sep. 26, 2003, which issued as U.S. Pat. No. 7,306,792 on Dec. 11, 2007, which is a national phase of International Application No. PCT/US02/09432, filed Mar. 27, 2002, which claims priority under 35 U.S.C. §119(e) from U.S. Provisional Patent Application Ser. Nos. 60/279,051, filed Mar. 27, 2001 and Ser. No. 60/311,373, filed Aug. 10, 2001, each of which are incorporated by reference in their entireties.

The research leading to the present invention was supported, in part, by National Cancer Institute through grant CA 68498. Accordingly, the U.S. government has certain rights in the invention.

FIELD OF THE INVENTION

The present invention relates to viral vector therapies for cancer, particularly to induce apoptosis of tumor cells in a specific manner, relative to normal cells in vivo.

BACKGROUND OF THE INVENTION

Cancer gene therapy would benefit greatly from the availability of a vector that has a high efficiency of gene expression and the ability to target tumors. A number of transfection systems have been developed to deliver heterologous genes into in vivo tumors to investigate cancer gene therapy, but all have limitations. For example, retroviral vectors have been used for gene delivery because they mediate stable gene transfer with a low potential for immunogenicity; however, transfer efficiencies are relatively low (see, e.g., Di lanni et al. J. Hematother. Stem. Cell Res., 1999, 8:645-652; Morling et al., Gene Ther., 1995, 2:504-508; Lam et al., Hum. Gene Ther., 1996, 7:1415-1422; Kume et al., Stem Cells, 1999, 17:226-232) and germ line modification is a potential problem (see Thompson, Science, 1992, 257: 1854). In addition, retroviral vectors, with few exceptions, are susceptible to lysis by serum components in human blood (see Miyao et al., Hum Gene Ther, 1997, 8:1575-1583; Russell et al., Hum Gene Ther, 1995, 6:635-641 and Rother et al., J Exp Med, 1995, 182:1345-55). This greatly limits their in vivo applications. Adenoviral vectors appear to be more efficient for gene transfer in vivo, but these vectors may be used only in a localized manner, because they lack the ability to be delivered via the bloodstream (see Duncan et al., J Gen Virol., 1978, 40:45-61; Alemany et al., J Gen Virol., 2000, 81 Pt 11:2605-2609 and Alemany et al., Nat. Biotechnol., 2000, 18:723-727), and may cause toxicity to patients due to the highly immunogenic properties of adenoviral proteins (see Ginsberg, Bulletin of the New York Acad. Med., 1996, 73:53-58 and Sparer et al., J. Virol., 1997. 71:2277-2284).

Despite these advances, cancer continues to be a major public health problem requiring new solutions. Current efforts at developing therapeutic vectors founder on problems of vector safety and expression efficacy of the therapeutic gene.

Many properties of alphavirus vectors make them a desirable alternative to other virus-derived gene delivery systems being developed, including the ability to (i) rapidly engineer expression constructs, (ii) produce high-titered stocks of infectious particles, (iii) infect non-dividing cells, and (iv) attain high levels of expression (Strauss and Strauss, Microbiol. Rev. 1994, 58:491-562; Liljeström et al., Biotechnology 1991, 9:1356-1361; Bredenbeek et al., Semin. Virol. 1992, 3:297-310; Xiong et al., Science 1993, 243:1188-1191).

Defective Sindbis viral vectors have been used to protect mammals from protozoan parasites, helminth parasites, ectoparasites, fungi, bacteria, and viruses (PCT Publication No. WO 94/17813).

A cDNA encoding Venezuelan Equine Encephalitis (VEE) and methods of preparing attenuated Togaviruses have been described (U.S. Pat. No. 5,185,440). Infectious Sindbis virus vectors have been prepared with heterologous sequences inserted into the structural region of the genome (U.S. Pat. No. 5,217,879). In addition, RNA vectors based on the Sindbis Defective Interfering (DI) particles with heterologous sequences have also been described (U.S. Pat. No. 5,091,309). Alphaviruses, specifically the Semliki Forest Virus, were used medically to deliver exogenous RNA encoding heterologous genes, e.g., an antigenic epitope or determinant (PCT Publications No. WO 95/27069 and WO 95/07994). Vectors for enhanced expression of heterologous sequences downstream from an alphavirus base sequence have been also disclosed (PCT Publication No. WO 95/31565). Alphavirus-based vectors were also used for protein production or expression of protein sequences for immunization (PCT Publication No. WO 92/10578). A cDNA construct for alphavirus vectors may be introduced and transcribed in animal or human cells (PCT Publication No. WO 95/27044).

Sindbis virus is a member of the alphavirus genus and has been studied extensively since its discovery in various parts of the world beginning in 1953 (see Taylor et al., Egypt. Med. Assoc., 1953, 36:489-494; Taylor et al., Am. J. Trop. Med. Hyg, 1955, 4:844-862; and Shah et al., Ind. J. Med. Res, 1960, 48:300-308). Like many other alphaviruses, Sindbis virus is transmitted to vertebrate hosts from mosquitos. Alphavirus virions consist of a nucleocapsid, wrapped inside a lipid bilayer, upon which the envelope proteins are displayed. The envelope proteins mediate binding to host cell receptors, leading to the endocytosis of the virion. Upon endocytosis, the nucleocapsid, a complex of the capsid protein and the genomic viral RNA, is deposited into the cytoplasm of the host cell. The Sindbis virus genome is a single-stranded 49S RNA of 11703 nt (Strauss et al., 1984, Virology, 133: 92-110), capped at the 5' terminus and polyadenylated at the 3' terminus. The genomic RNA is of (+)-sense, is infectious, and serves as mRNA in the infected cell. Translation of the genomic RNA gives rise to the nonstructural proteins, nsP1, nsP2, nsP3, and nsP4, which are produced as polyproteins and are proteolytically processed. Early during infection, the nonstructural proteins, perhaps in association with host factors, use the genomic (+)-sense RNA as template to make a full-length, complementary (−) strand RNA. The (−) strand is template for synthesis of full-length genomic RNA. An internal promoter on the (−) strand is used for transcription of a subgenomic 26S mRNA which is co-linear with the 3' terminal one-third of the genomic RNA. This 26S subgenomic mRNA is translated to produce a structural polyprotein that undergoes co-translational and post-translational cleavages to produce the structural proteins: C (capsid), E2, and E1 (envelope). The capsid protein C encapsidates the genomic RNA to form nucleocapsids. These interact with the cytoplasmic domain of the cell surface-bound viral envelope proteins, resulting in the envelopment of the nucleocapsid inside a membrane bilayer containing the envelope proteins, and the budding of progeny virions out of the infected cell. Sindbis virus infection has been shown to induce apoptosis in a host cell (Levine et al., Nature, 1993, 361; 739-742; Jan and Griffin, J. Virol., 1999, 73:10296-10302).

Although gene transduction based on Sindbis virus has been well-studied in vitro (see Straus et al., Microbiol. Rev., 1994, 58: 491-562; Altman-Hamamdzic et al., Gene Ther., 1997, 4; 815-822; Gwag et al., Mole. Brain Research., 1998, 63: 53-61; Bredenbeek et al., J Virol, 1993, 67; 6439-6446; Liljestrom et al., Biotechnology, 1991, 9: 1356-1361; Piper et al., *Meth. Cell Biol.*, 1994, 43:55-78; and Grusby et al., Proc Natl. Acad. Sci. USA., 1993, 90:3913-3917) and there are several reports of in vivo Sindbis virus gene transfer to the central nervous system (Duncan et al., J Gen Virol., 1978, 40:45-61; Alemany et al., J Gen Virol., 2000, 81 Pt 11:2605-2609; and Alemany et al., Nat. Biotechnol., 2000, 18:723-727) as well as to antigen presenting cells (see Tsuji et al., J Virol, 1998, 72:6907-6910; Hariharan et al., J Virol, 1998, 72:950-958; Pugachev et al., Virology, 1995, 212:587-594; and Xiong et al., Science, 1989, 243: 1188-1191), in vivo use of Sindbis virus system has been rather limited.

However, a major drawback to the use of Sindbis virus-based vectors was the fact that these vectors were thought (prior to this invention) to lack useful target cell specificity. For mammalian cells, at least one Sindbis virus receptor is a protein previously identified as the high affinity laminin receptor (HALR), whose wide distribution and highly conserved nature may be in part responsible for the broad host range of the virus (Strauss and Strauss, 1994, supra; Wang et al., J. Virol. 1992, 66:4992-5001). It was therefore thought desirable to alter the tropism of the Sindbis virus vectors to permit gene delivery specifically to certain target cell types (see PCT Publication No. WO 98/44132). Such alteration of tropism was suggested to require both the ablation of endogenous viral tropism and the introduction of novel tropism, e.g., by engineering a chimeric viral envelope protein containing an IgG binding domain of protein A.

In the mature Sindbis virus virion, a (+)-sense viral genomic RNA is complexed with capsid protein C to form icosahedral nucleocapsid that is surrounded by lipid bilayer in which two integral membrane glycoproteins, E1 and E2 are embedded (Strauss and Strauss, 1994, supra). Although E1 and E2 form a heterodimer that functions as a unit, the E2 domain appears to be particularly important for binding to cells. Monoclonal antibodies (mAbs) capable of neutralizing virus infectivity are usually E2 specific, and mutations in E2, rather than E1, are more often associated with altered host range and virulence (Stanley et al., J. Virol. 1985, 56:110-119; Olmsted et al., Virology 1986, 148:245-254; Polo et al., J. Virol. 1988, 62:2124:2133; Lustig et al., J. Virol., 1988, 62:2329-2336). Also, a Sindbis virus mutant was identified which contained an insertion in E2 and exhibited defective binding to mammalian cells (Dubuisson et al., J. Virol. 1993, 67:3363-3374).

In summary, there remains a need in the art for an effective treatment for cancer. In particular, the art needs an effective therapy that specifically targets tumor cells for destruction without significant adverse consequences for normal cells. The present invention addresses these and other needs in the art.

SUMMARY OF THE INVENTION

The present invention provides a novel method for treating a mammal (e.g., human) suffering from a tumor that expresses greater levels of high affinity laminin receptor (HALR) compared to normal cells of the same lineage. The method of the invention comprises administering to a mammal harboring such a tumor an amount of a vector effective to treat the tumor, wherein the vector has a preferential affinity for HALR. Preferably, the vector is a virus-based vector. As disclosed herein, the preferred virus-based vector for use in the method of the invention is an alphavirus-based vector (e.g., a replication defective alphavirus-based vector), more preferably, a replication defective Sindbis virus-based vector.

As disclosed herein, in addition to alphavirus-based vectors which possess natural affinity for HALR and natural apoptosis-inducing functions, the vectors of the invention can be derived from any particle or virus that can be effectively modified to have a preferential affinity for HALR and to possess an anti-tumor activity. Accordingly, in a separate embodiment, the instant invention includes a method for treating a mammal suffering from a tumor using the vector which has a preferential affinity for HALR and encodes an anti-tumor gene. As disclosed herein, such anti-tumor gene can be a suicide gene, an apoptosis-inducing gene, a tumor suppressor gene, an oncogene antagonist gene, an immunostimulatory gene, a tumor suppressor effector gene, an antisense oligonucleotide-encoding sequence, a ribozyme-encoding sequence, or an immunogenic peptide-encoding sequence. In a preferred embodiment, such anti-tumor gene is an apoptosis-inducing gene or a cytokine-encoding gene.

In another embodiment, the present invention provides a method for treating a mammal (e.g., human) suffering from a tumor using an alphavirus-based vector, wherein the vector is not modified to specifically target the tumor. Preferably, the alphavirus-based vector is a Sindbis virus-based vector, most preferably, a replication defective Sindbis virus-based vector. As disclosed herein, the alphavirus-based vector can be modified to encode a heterologous anti-tumor gene.

The instant invention also includes a method for treating a mammal suffering from a tumor using the alphavirus-based vector which is modified to target a specific tumor. Thus, as disclosed herein, the vector for use in the method of the invention can be modified to encode a molecule which specifically interacts with a ligand present in tumor cells. According to a specific embodiment, the vector can be modified to encode, for example, a chimeric envelope protein containing a tumor-specific receptor-binding sequence, a peptide mimetic with affinity for a tumor-specific binding site, an immunoglobilin molecule or its fragment recognizing a tumor-specific antigen, or the IgG-binding domain of protein A that can be administered together with anti-viral receptor (e.g., anti-HALR) antibodies.

As specified in the Detailed Description and Examples, the methods according to the present invention can be used to treat all kinds of tumors and metastases. In a specific embodiment, the method according to the present invention is used to treat solid tumors, in particular, hepatic carcinoma, melanoma, epidermoid carcinoma, pancreatic cancer, brain malignancies (such as neuroblastoma, glioblastoma, glioma, medulloblastoma, astrocytoma, acoustic neuroma, oligodendroglioma, and meningioma), breast cancer, lung cancer (such as small cell lung and non-small cell lung cancer), ovarian adenocarcinoma, colon cancer, prostate cancer, bladder cancer, and renal cancer.

According to the present invention, the anti-tumor vector is preferably administered to the mammal (e.g., human) parenterally, e.g., intraperitoneally.

The invention further provides the evidence that the disclosed methods of treating tumors, especially with alphaviral vectors, are particularly efficient if the mammal undergoing treatment has at least a partially functional immune system. In a specific embodiment, the invention provides the evidence that the methods of treating tumors using Sindbis virus-based vectors are more efficient in the presence of functional natural killer (NK) cells.

Further provided herein is a method for killing a tumor cell (either in vivo or in vitro) comprising contacting the tumor cell with an amount of a vector effective to kill the tumor cell, wherein the vector has a preferential affinity for HALR and may or may not encode a heterologous anti-tumor gene. Preferably, the vector is a replication defective alphavirus-based vector, more preferably a replication defective Sindbis virus-based vector.

In conjunction with the methods disclosed herein, the present invention advantageously provides pharmaceutical compositions for treating a mammal suffering from a tumor comprising a vector and a pharmaceutically acceptable carrier or diluent, wherein the vector has a preferential affinity for HALR and is effective to kill a tumor, with the proviso that, if the vector is an alphavirus-based vector, it has not been modified to target a tumor-specific cellular determinant. These pharmaceutical compositions can be used to treat all kinds of tumors and metastases that are characterized by elevated levels of HALR expression compared to normal cells of the same lineage. As disclosed herein, the vectors of the present invention can be derived from particles or viruses that have no natural affinity for HALR (e.g., retroviruses or adenoviruses) by modifying their targeting molecules to include the HALR-binding domain(s) of the Sindbis virus envelope protein(s). Alternatively, the vector can be an alphavirus-based vector, most preferably a replication defective Sindbis virus-based vector, which has its natural targeting properties and has not been modified to target a tumor-specific cellular determinant.

The vectors for use in the pharmaceutical compositions of the invention can be modified to include a heterologous anti-tumor gene such as but not limited to a suicide gene, an apoptosis-inducing gene, a tumor suppressor gene, an oncogene antagonist gene, an immuno-stimulatory gene, a tumor suppressor effector gene, an antisense oligonucleotide-encoding sequence, a ribozyme-encoding sequence, or an immunogenic peptide-encoding sequence. In a preferred embodiment, such anti-tumor gene is an apoptosis-inducing gene or a cytokine-encoding gene.

The compositions of the invention can be used to treat various solid tumors, in particular, hepatic carcinoma, melanoma, epidermoid carcinoma, pancreatic cancer, brain malignancies (such as neuroblastoma, glioblastoma, glioma, medulloblastoma, astrocytoma, acoustic neuroma, oligodendroglioma, and meningioma), breast cancer, lung cancer (such as small cell lung and non-small cell lung cancer), ovarian adenocarcinoma, colon cancer, prostate cancer, bladder cancer, and renal cancer.

As disclosed in a separate embodiment, the compositions of the invention, especially the compositions comprising alphaviral vectors, are particularly efficient if administered to mammals (e.g., via a parenteral route) having at least a partially functional immune system, preferably the immune system comprising functional natural killer (NK) cells.

The present invention meets these and other objects of the invention, as set forth in greater detail in the Detailed Description and Examples, including the accompanying Drawings.

DETAILED DESCRIPTION OF THE INVENTION

Figure 1:
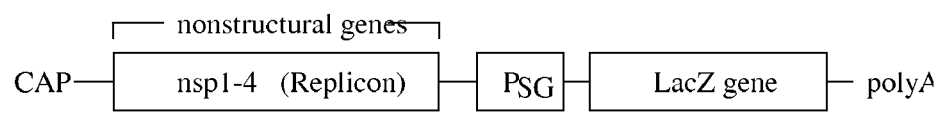
FIG. 1. Schematic representation of the Sindbis virus-based expression and helper vectors. SinRep/LacZ is a Sindbis virus-based expression vector, which contains the packaging signal, nonstructural protein genes for replicating the RNA transcript and the LacZ gene. DH-BB is a parental helper plasmid that contains the genes for the structural proteins (capsid, E3, E2, 6K and E1) required for packaging of the Sindbis viral genome. Abbreviations: PSG, Sindbis virus subgenomic promoter; C, capsid; nsp 1-4, nonstructural protein genes 1-4; poly A, polyadenylation signal. Not shown are SinRep/Luc and SinRep/IL12 vectors, which are generally similar to SinRep/LacZ. SinRep/Luc comprises a DNA fragment encoding the firefly luciferase gene (Luc) in place of LacZ (subcloned into the Xba I site of SinRep vector). SinRep/IL12 comprises murine IL12 α-subunit and β-subunit genes (subcloned into the Mlu I site and the Stu I site downstream of the Sph I site) and a second subgenomic promoter DNA downstream of the original subgenomic promoter of SinRep/LacZ.
Figure 1:
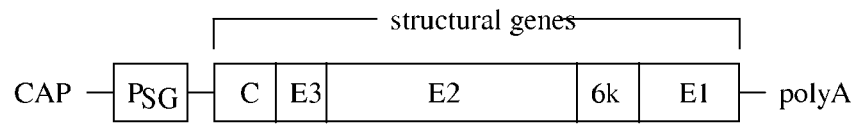

The present invention advantageously harnesses simple alphavirus vectors and existing anti-tumor vectors for effective anti-tumor therapy. The invention is based, in part, on the unexpected discovery that a replication defective alphavirus vector is an effective anti-cancer therapeutic. Accordingly, the invention provides a method for treating a mammal (e.g., human) suffering from a tumor using an alphavirus-based vector, wherein the vector is not modified to specifically target the tumor. Preferably, the alphavirus-based vector is a Sindbis virus-based vector, most preferably, a replication defective Sindbis virus-based vector.

Specifically, the present invention is based, in part, on the observation that a replication defective Sindbis virus vector, in which the structural genes are deleted and substituted with, e.g., a heterologous reporter gene (such as β-galactosidase or luciferase) operatively associated with a Sindbis virus subgenomic promoter proximal to the 5' end of the coding sequence, and a polyadenylation signal at the 3' end of the coding sequence, is able to effectively target tumor cells in vivo. It has been unexpectedly discovered that Sindbis vectors, unmodified with respect to targeting, display high affinity for tumor cells growing in vitro or in vivo and are capable of efficiently inducing their death leading to tumor regression and long term survival of experimental tumor-bearing animals (even in the absence of any heterologous anti-tumor gene payload).

In this respect, the present invention provides an unexpected and advantageous departure from standard gene therapy using viral vectors. In gene therapy, the vector is a vehicle for delivering a therapeutic gene. In the case of cancer gene therapy, the therapeutic gene adversely affects tumor cells. Examples of typical therapeutic genes for gene therapy of cancer ("tumor therapeutic genes") include, but are not limited to, tumor suppressors (e.g., p53 and RB); anti-oncogenic intracellular antibodies (e.g., anti-Ras and anti-Raf antibodies); a protein capable of enzymatically converting a prodrug into a compound that is toxic to the tumor (e.g., herpes simplex virus thymidine kinase [HSV-tk], which forms a toxin with ganciclovir; varicella zoster virus thymidine kinase [VZV-tk], which forms a toxin with 6-methoxypurine arabinoside; or a bacterial cytosine deaminase, which forms a toxin with 5-fluorocytosine); or an immuno-stimulatory protein capable of enhancing anti-tumor immunity (e.g., flt-3 ligand, GM-CSF, IL-2, IL-7, IL-12, and IL-13). Although the presence of any such "tumor therapeutic gene" in the vectors of the invention can enhance the anti-tumor effect (as shown, e.g., by comparing a vector encoding a marker gene [LacZ] and a vector encoding a cytokine gene [IL12]; see Example 1, infra), it is disclosed herein that the presence of such gene is not necessary to obtain the therapeutic effect if the vector is an alphavirus vector that is naturally apoptotic. Accordingly, the Sindbis virus-based vectors of the invention need not carry any heterologous coding sequence at all. In a specific embodiment, however, the therapeutically active Sindbis virus vectors of the invention encode a heterologous marker gene, such as β-galactosidase, luciferase, or Hygromycin-EGFP. In another embodiment, these vectors encode a heterologous anti-tumor therapeutic gene, such as an apoptosis-inducing gene or a cytokine-encoding gene.

The instant invention takes advantage, for the first time, of the natural affinity of an alphavirus, particularly Sindbis virus, for tumor cells, in particular, for tumor cells that express higher levels of high affinity laminin receptors (HALRs), as compared to normal cells of the same lineage. The term "high affinity laminin receptor" or "HALR" has its ordinary meaning in the art, i.e., the Mr 67,000 laminin receptor that can function as the receptor for Sindbis virus entry into cells (see Wang et al., J. Virol. 1992, 66:4992-5001; Strauss et al., Arch. Virol. Suppl. 1994, 9:473-84). Based on this observation, it is clear that modifying any vector to target it to HALR is within the scope of the invention.

Accordingly, the present invention provides a method for treating a mammal (e.g., human) suffering from a tumor that expresses greater levels of high affinity laminin receptor (HALR) compared to normal cells of the same lineage. The method comprises administering to a mammal harboring such a tumor an amount of a vector effective to treat the tumor, wherein the vector has a preferential affinity for HALR. The vector can be derived from any particle or virus that can be effectively modified to have a preferential affinity for HALR and to possess an anti-tumor activity.

While not bound by any particular theory, three sets of observations, which have not been previously considered together, may account for the remarkable anti-tumor efficiency of Sindbis vector-based therapy of the present invention. First, the HALR can function as the receptor for Sindbis virus entry into cells of most species (Wang et al., J. Virol., 1992, 66:4992-5001; and Strauss et al., Arch. Virol. Suppl., 1994, 9:473-484). Second, it is widely recognized that expression of the HALR (Mr 67,000) is markedly elevated in many types of cancers (Menard et al., Breast Cancer Res. Treat, 1998, 52:137-145). In fact, a significant correlation has been established between the increased expression of Mr 67,000 HALR and cancers of the breast (Menard et al., 1998, supra; Paolo Viacava et al., J. Pathol., 1997, 182: 36-44; Martignone et al., J. Natl. Cancer Inst., 1993, 85:398-402), thyroid (Basolo et al., Clin. Cancer Res., 1996, 2:1777-1780), colon (Sanjuan et al., J Pathol., 1996, 179:376-380), prostate (Menard S et al., Breast Cancer Res. Treat, 1998, 52:137-145), stomach (de Manzoni et al., Jpn J Clin. Oncol., 1998, 28:534-537), pancreas (Pelosi et al., J Pathol., 1997, 183:62-69), ovary (Menard et al., Breast Cancer Res. Treat, 1998, 52:137-145; and van den Brule et al., Eur J Cancer, 1996, 32A:1598-1602.), melanocytes (Taraboletti et al., J Natl. Cancer Inst., 1993, 85:235-240), lung (Menard et al., Breast Cancer Res. Treat, 1998, 52:137-145), liver (Ozaki et al., Gut, 1998, 43:837-842), endometrium, and uterus (van den Brule et al., Hum Pathol, 1996, 27:1185-1191). Indeed, data on more than 4000 cases of different tumors from diverse organs studied by immunohistochemistry are all concordant with a role for HALR in invasiveness, metastasis, and tumor growth (Menard et al., Breast Cancer Res. Treat., 1998, 52:137-145). Sindbis vectors, which are naturally blood-borne, can easily travel through the circulation and specifically home to growing and metastatic tumors expressing increased levels of HALR. Finally, Sindbis virus is well known to be highly apoptotic for mammalian cells (Levine et al., Nature 1993, 739-742; Jan et al. J Virol., 1999; 10296-10302; Jan et al. J Virol., 2000 6425-6432). Cell death begins within a few hours of infection and by 48-96 hours virtually all infected cells are dead (Sawai et al., Mol Genet Metab. 1999, 67:36-42; Griffin et al., Ann. Rev., 1997, Microbiol. 51:565-592).

Although the evidence of HALR involvement in Sindbis virus-mediated tumor cell infection is compelling, it is possible that Sindbis virus-based vectors as well as other alphavirus-based vectors of the invention also interact with other tumor-specific cellular determinants (e.g., receptors). In other words, while the disclosed vectors preferentially target to tumor cells that express increased levels of HALRs, this may reflect a characteristic of the cell and need not be the mechanism by which the vector infects the cell. The present invention encompasses any other such mechanisms involved in alphavirus-mediated infection and cytotoxicity of tumor cells.

As noted above, vectors of the invention can also carry payloads of one or several genes, which could be used to enhance the cytotoxic potential, if necessary. Thus, the invention further relates to using vectors for delivery of anti-tumor therapeutic genes.

Importantly, compared to tumor cells, vectors of the present invention, especially Sindbis vectors, do not appear to infect normal cells to the same extent in vivo. This allows for a differential effect in vector therapy, e.g., where infection by Sindbis vector with resulting death of tumor cells can lead to tumor elimination without apparent deleterious effects to other tissues and organs of the treated subjects. This phenomenon may be explained by the observation that an increased number of HALRs in tumors versus normal cells leads to a high number of exposed or unoccupied receptors on tumor cells (Liotta, L. A. Cancer Research, 1986, 46:1-7; Aznavoorian et al., 1992, Molecular Aspects of Tumor Cell Invasion and Metastasis, pp. 1368-1383). For example, it has been demonstrated that breast carcinoma and colon carcinoma tissues contain a higher number of exposed (unoccupied) HALR receptors compared to benign lesions (Liotta et al., 1985, Exp. Cell Res., 156:117-26; Barsky et al., Breast Cancer Res. Treat., 1984, 4:181-188; Terranova et al., Proc. Natl. Acad. Sci. USA, 1983, 80: 444-448). These excess unoccupied HALR receptors on tumor cells, which are not found in normal cells, may be available for Sindbis virus binding, infection, and induction of cell death.

Recognition that replication defective Sindbis virus vectors with unmodified cell specificity have intrinsic anti-tumor activity allows to take advantage of the numerous other important properties of Sindbis vectors. Thus, Sindbis vectors show extremely high efficiency of gene transfer. They are (+)-stranded RNA viruses, which through a process of amplification in the cytoplasm of infected cells can express 105 or more active RNA species per cell within a few hours after infection. This level of RNA amplification also allows for very high levels of expression of the transferred gene products, which would, in turn, lead to prolonged expression where it not for the apoptotic nature of the virus (Levine et al., 1993, Nature, 361: 739-742; Jan et al., J Virol., 1999, 73: 10296-10302; Jan et al., J Virol., 2000, 74: 6425-6432; Balachandran et al., J. Virol., 2000, 74: 1513-1523). Based on recommendations for the handling of alphaviruses and other arboviruses in the laboratory (The Subcommittee on Arbovirus Laboratory Safety of the American Committee on Arthropod-Borne Viruses, Am. J. Trop. Med. Hyg, 1980, 29:1359-1381), Sindbis is considered fairly safe. The majority of alphaviruses require Level 3 practice and containment and/or vaccination, whereas Sindbis requires only Level 2 practices and containment, which is assigned to viruses whose infection result either in no disease or in disease which is self-limited. Replication defective Sindbis vectors derived from Sindbis viruses, as exemplified herein, can be considered even safer as their capacity to infect and replicate to cause viremia or disease is virtually non-existent. The capacity to infect and replicate to cause viremia can only be reacquired through recombination, which can be minimized and monitored. Sindbis vectors also avoid potential complications associated with chromosomal integration (Xiong et al., Science, 1989, 243: 1188-1191). Recent methods have added substantial ease to engineering new Sindbis vector constructs capable of nonreplicative infection and further enhanced safety aspects of the vector (Straus et al., Microbiol. Rev., 1994, 58: 491-562, 1994). Because Sindbis virus is a blood-borne virus (Turrell, 1988, CRC Press, Inc. Boca Raton, Fla.) and can cross the blood-brain barrier (Altman-Hamamdzic et al., Gene Ther., 1997, 4; 815-822), vectors based on this virus are among the few available ones that are capable of migrating through the blood stream to reach all cells of the body. In this respect they hold an important advantage over many other vectors and can be used, for example, to treat brain malignancies (such as neuroblastoma, glioblastoma, glioma, medulloblastoma, astrocytoma, acoustic neuroma, oligodendroglioma, and meningioma).

In addition to "naturally targeted" alphavirus-based vectors, the present invention also discloses tumor necrosis-inducing alphavirus-based vectors, which carry more specific tumor targeting molecules, such as, for example, chimeric envelope proteins containing a tumor-specific receptor-binding sequence, a peptide mimetic with affinity for a tumor-specific binding site, an immunoglobulin molecule/fragment recognizing a tumor-specific antigen, or the IgG-binding domain of protein A that can be administered together with anti-viral receptor (e.g., anti-HALR) antibodies. In a specific embodiment, the present invention provides Sindbis-based vectors, which are specifically targeted to tumor cells due to the presence of chimeric E2 envelope proteins modified, e.g., to include one or more of the five highly homologous 58 amino acid-long Fc IgG-binding domains of protein A, i.e., domains E, D, A, B, C, or domain Z, an engineered analog of the B domain containing two amino acid substitutions Ala1->Val and Gly29->Ala (see commonly owned PCT Publication No. WO 98/44132; Uhlen et al., J. Biol. Chem., 1984, 259:1695; Moks et al., Eur. J. Biochem., 1986, 156:637-43). In a further embodiment, the invention provides Sindbis virus-based vectors comprising chimeric envelope proteins, which are modified to include a domain capable of binding to other kinds of determinants expressed at high levels on the surface of a target tumor cell (e.g., EGF receptors overexpressed in many cancer cells or $\alpha_v\beta_3$ integrins overexpressed on melanoma cells; see Dmitriev et al., J. Virol., 2000, 6875-84; Bonnie et al., Virol., 2000, 269:7-17) or, alternatively, a domain interacting with receptors expressed at a relatively higher level in a specific cancer cell type (e.g., ductal epithelial cells in breast cancer). Thus, in a particular embodiment, the present invention provides Sindbis virus-based vectors comprising chimeric E2 envelope proteins modified by insertion of the α- and β-hCG sequences (as disclosed by the present inventors in Sawai and Meruelo, 1998, Biochem. Biophys. Res. Com., 248:315-323) and having the ability to selectively infect and transfer a reporter gene to choriocarcinoma cells as well as other tumor cells bearing LH/CG receptors, but not to cells lacking these receptors.

In contrast to many other viral vectors comprising chimeric targeting molecules, the alphavirus-based vectors of the present invention comprising chimeric E2 proteins are highly tolerant to the specific structure and/or size of a heterologous targeting fragment inserted in the E2 envelope protein. This property is likely to be attributed to the separation of the functional roles between E2 and E1 proteins in cell targeting and fusion. Specifically, extensive experimentation has established that E2 protein is involved primarily in binding of the virus to the cell surface receptors, while viral entry involves low pH-induced exposure of the fusion domain in E1 followed by fusion with the endosomal membrane, endocytosis in clathrin-coated vesicles, and transfer to endosomes (Hoekstra et al., Biosci Rep., 1989, 9:273-305; Kielian and Helnius, pp. 91-119, In S. Schlesinger and M. J. Schlesinger (ed.), *The Togaviridae and Flaviviridae.* Plenum Publishing Corp., New York, 1986; Kielian et al., J. Virol., 1990, 64:4614-24; Marsh, Biochem J., 1984, 218:1-10; Stegmann et al., Annu. Rev. Biophys. Biophys. Chem., 1989, 18:187-211; Helenius et al., J. Cell Biol., 1980, 84:404-20; Marsh et al., Cell, 1983, 32: 931-940).

Tumor-specific targets for the chimeric envelope proteins of the vectors of the instant invention include without limitation any tumor cell-specific protein, peptide, oligonucleotide, lipid, polysaccharide, and a small molecule ligand.

Most importantly, the present invention is not limited to naturally targeted alphavirus-derived anti-tumor vectors. As specified herein, using methods that are well known in the art, the vectors of the present invention can be derived from viruses (such as retroviruses, adenoviruses, adeno-associated viruses, lentiviruses, herpes viruses, vaccinia viruses, baculoviruses, papilloma viruses, etc.) or non-viral particles (such as liposomes, microspheres, protein matrices, etc.) that have no natural affinity for HALR by modifying their targeting molecules to include the HALR-binding domain(s) of the Sindbis virus envelope protein(s) (preferably, the HALR-binding domain of E2), or an immunoglobilin fragment recognizing HALR, or the IgG-binding domain of protein A that can be administered together with anti-HALR antibodies, or laminin (or the HALR binding portion thereof). For example, in a specific embodiment, the invention provides anti-tumor adenovirus-based vectors, which have the sequence encoding the terminal knob of the capsid protein fiber deleted to ablate the natural binding to CAR and other adenovirus receptors, while simultaneously inserting the sequence responsible for HALR binding (see, e.g., Alemany et al., Nat. Biotechnol., 2000, 18:723-727). In an alternative embodiment, tumor-specific adenovirus-based vectors are administered together with a recombinantly produced bispecific hybrid adapter protein consisting of the amino-terminal extracellular domain of the CAR protein (see, e.g., Dmitriev et al., J. Virol., 2000, 74:6875-84; Ebbinghaus et al., J. Virol., 2001, 75:480-489) and an HALR-binding domain of Sindbis virus E2, or an immunoglobilin fragment recognizing HALR, or the IgG-binding domain of protein A that can be administered together with anti-HALR antibodies. In another embodiment, the invention similarly provides retrovirus-based anti-tumor vectors which have altered targeting properties due to replacement of the receptor-binding region of env protein (e.g., N-terminal region of env in murine leukemia retrovirus (MLV)-based vectors) with the HALR-binding domain (see, e.g., Ohno and Meruelo, Biochem. Mol. Med., 1997, 62:123-127).

Taken together, the invention advantageously provides a method for treating a mammal suffering from a tumor, in which the cells of the tumor express greater levels of HALR compared to normal cells of the same lineage. The different levels of HALRs result in target-mediated delivery, i.e., preferential binding of vectors of the invention to tumor cells. "Greater levels" of expression generally refer herein to levels that are expressed by tumor cells (as compared to non-tumor cells) and result in such preferential binding, e.g., at least a 3-fold greater binding, preferably at least a 30-fold greater binding, most preferably at least a 300-fold greater binding. The increased level of expression in tumor cells can be evaluated on an absolute scale, i.e., relative to any other HALR expressing non-tumor cells described, or on a relative scale, i.e., relative to the level expressed by untransformed cells in the same lineage as the transformed cancer cells (e.g., melanocytes in the case of melanoma; hepatocytes in the case of hepatic carcinoma; ovarian endothelial cells in the case of ovarian adenocarcinoma, renal endothelial or epithelial cells in the case of renal carcinoma).

General Definitions

The terms "vector", "cloning vector", "expression vector", and "helper vector" mean the vehicle by which a DNA or RNA sequence (e.g., a foreign gene) can be introduced into a host cell, so as to promote expression (e.g., transcription and/or translation) of the introduced sequence. Vectors include plasmids, phages, viruses, etc. As used herein with respect to viral vectors of the invention, "expression vector" is used most commonly to refer to a vector that is capable of infecting a host cell, while the term "helper vector" is used to refer to a vector that is able to mediate proper packaging of the "expression vector" into a virus-like particle.

As used herein, the term "heterologous sequence or gene" means a nucleic acid (RNA or DNA) sequence, which is not naturally found in association with the nucleic acid sequences of the specified molecule, e.g., an alphavirus genome. Similarly, the term "heterologous protein or peptide" means a protein, peptide and/or amino acid sequence not naturally encoded in an alphavirus genome. Within the meaning of the present invention, a heterologous gene contained in the aplhavirus-based vectors is typically of a non-viral origin. However, the term can also include aphavirus sequences which have been altered by human manipulation to cause changes (e.g., nucleic acid deletions, substitutions, and/or additions) in the primary nucleic acid sequence and/or positioning in the native (e.g., naturally occurring) virus molecule. Preferred heterologous genes of the instant invention include, but are not limited to, reporter genes (such as β-galactosidase and luciferase genes), anti-tumor genes (such as suicide genes, apoptosis-inducing genes, tumor suppressor genes, oncogene antagonist genes, immunostimulatory genes, tumor suppressor effector genes, antisense oligonucleotide-encoding sequences, ribozyme-encoding sequences, or immunogenic peptide-encoding sequences), and genes encoding tumor-targeting molecules (such as genes encoding chimeric envelope proteins containing a tumor-specific receptor-binding sequence, sequences encoding peptide mimetics with affinity for tumor-specific binding sites, genes encoding immunoglobulin molecules/fragments recognizing tumor-specific antigens, or genes encoding the IgG-binding domain of protein A that can be administered together with anti-viral receptor [e.g., anti-HALR] antibodies).

As used herein, the term "infectious", when used to describe an alphavirus-based RNA molecule, means an RNA molecule which is self-replicating and provides for transcription in a host cell. The term "replication", when used in conjunction with an alphavirus genomic RNA or a recombinant alphavirus-based vector RNA molecule mean production of full-length equivalents of (+)-strand RNA using (−)-strand RNA as a template.

As used herein, the term "transfection" is understood to include any means, such as, but not limited to, adsorption, microinjection, electroporation, lipofection and the like for introducing an exogenous nucleic acid molecule into a host cell. The term "transfected" or "transformed", when used to describe a cell, means a cell containing an exogenously introduced nucleic acid molecule and/or a cell whose genetic composition has been altered by the introduction of an exogenous nucleic acid molecule.

As used herein, the term "preferential binding" or "preferential affinity" refers to the ability of the viral vector to interact with a given cellular receptor (e.g., HALR) leading to an increased infection of cells expressing this receptor. It follows, that vectors of the present invention having preferential affinity for HALR receptors would particularly efficiently infect tumor cells which express increased numbers of HALRs.

As used herein, the term "tumor" refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, epidermoid carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, neuroglioma, and retinoblastoma. As noted above, the method of the invention depends on expression of HALRs by cells of the tumor targeted for treatment.

The term "tumor-specific cellular determinant" or "tumor-specific target" is used herein to broadly define any molecule on the surface of a tumor cell, which can be used for selective or preferential targeting of this cell by the vectors of the invention. Tumor-specific cellular determinants for the vectors of the instant invention include without limitation any tumor cell surface protein, peptide, oligonucleotide, lipid, polysaccharide, and a small molecule ligand. Preferred tumor-specific cellular determinants of the invention are tumor-specific membrane proteins such as ErbB receptors, Melan A [MART1], gp100, tyrosinase, TRP-1/gp 75, and TRP-2 (in melanoma); MAGE-1 and MAGE-3 (in bladder, head and neck, and non-small cell carcinoma); HPV EG and E7 proteins (in cervical cancer); Mucin [MUC-1] (in breast, pancreas, colon, and prostate cancers); prostate-specific antigen [PSA] (in prostate cancer); carcinoembryonic antigen [CEA] (in colon, breast, and gastrointestinal cancers), LH/CG receptor (in choriocarcinoma), and such shared tumor-specific antigens as MAGE-2, MAGE-4, MAGE-6, MAGE-10, MAGE-12, BAGE-1, CAGE-1,2,8, CAGE-3 to 7, LAGE-1, NY-ESO-1/LAGE-2, NA-88, GnTV, and TRP2-INT2, etc. HALRs as well as other determinants (e.g., EGF receptors or $\alpha_v\beta_3$ integrins), which are expressed at higher levels on the surface of certain tumor cells, as compared to normal cells of the same lineage, are also encompassed by the term "tumor-specific cellular determinant."

As used herein, the term "mammal" has its ordinary meaning, and specifically includes primates, and more specifically includes humans. Other mammals that may be treated for the presence of a tumor include, but are not limited to, canine, feline, rodent (racine, murine, lupine, etc.), equine, bovine, ovine, caprine, and porcine species.

The term "subject" as used herein refers to a vertebrate, preferably a mammal (e.g., rodent such as mouse). In particular, the term refers to humans.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log(i.e., an order of magnitude) preferably within a factor of two of a given value.

The term "treat" is used herein to mean to relieve or alleviate at least one symptom of a disease in a subject. Within the meaning of the present invention, the term "treat" may also mean to prolong the prepatency, i.e., the period between infection and clinical manifestation of a disease. The term "protect" is used herein to mean prevent or treat, or both, as appropriate, development or continuance of a disease in a subject. Within the meaning of the present invention, the disease is cancer.

The phrase "pharmaceutically acceptable", as used in connection with compositions of the invention, refers to molecular entities and other ingredients of such compositions that are physiologically tolerable and do not typically produce untoward reactions when administered to a human. Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

The term "therapeutically effective" applied to dose or amount refers to that quantity of a compound or pharmaceutical composition that is sufficient to result in a desired activity upon administration to a mammal in need thereof. As used herein with respect to viral vectors of the invention, the term "therapeutically effective amount/dose" refers to the amount/dose of a vector or pharmaceutical composition containing the vector that is sufficient to produce an effective anti-tumor response upon administration to a mammal.

The term "antibody" is used in the broadest sense and specifically covers not only native antibodies but also single monoclonal antibodies (including agonist and antagonist antibodies), antibody compositions with polyepitopic specificity, as well as antibody fragments (e.g., Fab, F(ab')$_2$, scFv and Fv), so long as they exhibit the desired biological activity.

The term "innate immunity" or "natural immunity" refers to innate immune responses that are not affected by prior contact with the antigen. The protective mechanisms of the innate immunity include, among others, natural killer (NK) cells, which destroy microbes and certain tumor cells, and attack certain virus infected cells, and the inflammatory response, which mobilizes leukocytes such as macrophages and dendritic cells to phagocytose invaders.

Vectors

Most preferred vectors of the invention are alphavirus-based vectors, in particular, replication defective naturally targeted Sindbis virus-based vectors. Other preferred vectors of the invention in vitro, in vivo, and ex vivo are viral vectors, such as retroviruses (including lentiviruses), herpes viruses, adenoviruses, adeno-associated viruses, vaccinia virus, papillomavirus, Epstein Barr virus (EBV), baculovirus, and other recombinant viruses with or modified to have the desirable cellular tropism, i.e., binding preferentially to the high affinity laminin receptor (HALR).

Methods for constructing and using viral vectors are known in the art (see, e.g., Miller and Rosman, BioTechniques 1992, 7:980-990). In accordance with the present invention there may be employed conventional molecular biology, microbiology, and recombinant DNA techniques within the skill of the art. Such techniques are well-known and are explained fully in the literature. See, e.g., Sambrook, Fritsch and Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), and Transgene (Strasbourg, France; adenoviral, vaccinia, retroviral, and lentiviral vectors).

Preferably, the viral vectors of the invention are replication defective, that is, they are unable to replicate autonomously in the target cell. Preferably, the replication defective virus is a minimal virus, i.e., it retains only the sequences of its genome which are necessary for target cell recognition and encapsidating the viral genome. Replication defective virus is not infective after introduction into a cell. Use of replication defective viral vectors allows for administration to cells in a specific, localized area, without concern that the vector can infect other cells. Thus, a specific tissue can be specifically targeted. In addition to replication defective alphavirus vectors, examples of particular vectors include, but are not limited to, defective herpes virus vectors (see, e.g., Kaplitt et al., Molec. Cell. Neurosci. 1991, 2:320-330; Patent Publication RD 371005 A; PCT Publications No. WO 94/21807 and WO 92/05263), defective adenovirus vectors (see, e.g., Stratford-Perricaudet et al., J. Clin. Invest. 1992, 90:626-630; La Salle et al., Science 1993, 259:988-990; PCT Publications No. WO 94/26914, WO 95/02697, WO 94/28938, WO 94/28152, WO 94/12649, WO 95/02697, and WO 96/22378), and defective adeno-associated virus vectors (Samulski et al., J. Virol. 1987, 61:3096-3101; Samulski et al., J. Virol. 1989, 63:3822-3828; Lebkowski et al., Mol. Cell. Biol. 1988, 8:3988-3996; PCT Publications No. WO 91/18088 and WO 93/09239; U.S. Pat. Nos. 4,797,368 and 5,139,941; European Publication No. EP 488 528).

As specified above, various strategies can be implemented to target vectors to the HALR, including but not limited to pseudotyping the viral vector by introducing an HALR binding sequence, e.g., a Sindbis virus E2 protein, into the virus; by modifying viral capsid or envelope proteins to contain an HALR binding sequence; by using a bi-specific reagent that binds to the vector and to HALR; or using combinations of these approaches.

Adenovirus-based vectors. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to using type 2 or type 5 human adenoviruses (Ad 2 or Ad 5) or adenoviruses of animal origin (see PCT Publication No. WO94/26914). Those adenoviruses of animal origin which can be used within the scope of the present invention include adenoviruses of canine, bovine, murine (e.g., Mav1 [Beard et al., Virology, 1990, 75:81]), ovine, porcine, avian, and simian (e.g., SAV) origin. Preferably, the adenovirus of animal origin is a canine adenovirus, more preferably a CAV2 adenovirus (e.g., Manhattan or A26/61 strain [ATCC Accession No. VR-800]). Various replication defective adenovirus and minimum adenovirus vectors have been described (PCT Publications No. WO94/26914, WO95/02697, WO94/28938, WO94/28152, WO94/12649, WO95/02697, WO96/22378). The replication defective recombinant adenoviruses according to the invention can be prepared by any technique known to the person skilled in the art (Levrero et al., Gene, 1991, 101:195; EP Publication No. 185 573; Graham, EMBO J., 1984, 3:2917; Graham et al., J. Gen. Virol., 1977, 36:59). Recombinant adenoviruses are recovered and purified using standard molecular biological techniques, which are well known to one of ordinary skill in the art.

Adeno-associated virus-based vectors. The adeno-associated viruses (AAV) are DNA viruses of relatively small size which can integrate, in a stable and site-specific manner, into the genome of the cells which they infect. They are able to infect a wide spectrum of cells without inducing any effects on cellular growth, morphology or differentiation, and they do not appear to be involved in human pathologies. The AAV genome has been cloned, sequenced and characterized. The use of vectors derived from the AAVs for transferring genes in vitro and in vivo has been described (see PCT Publications No. WO 91/18088 and WO 93/09239; U.S. Pat. Nos. 4,797,368 and 5,139,941; EP Publication No. 488 528). The replication defective recombinant AAVs according to the invention can be prepared by cotransfecting a plasmid containing the nucleic acid sequence of interest flanked by two AAV inverted terminal repeat (ITR) regions, and a plasmid carrying the AAV encapsidation genes (rep and cap genes), into a cell line which is infected with a human helper virus (e.g., an adenovirus). The AAV recombinants which are produced are then purified by standard techniques.

Retroviral vectors. In another embodiment, the invention provides retroviral vectors, e.g., as described in Mann et al., Cell 1983, 33:153; U.S. Pat. Nos. 4,650,764, 4,980,289, 5,124,263, and 5,399,346; Markowitz et al., J. Virol. 1988, 62:1120; EP Publications No. 453 242 and 178 220; Bernstein et al. Genet. Eng. 1985, 7:235; McCormick, BioTechnology 1985, 3:689; and Kuo et al., 1993, Blood, 82:845. The retroviruses are integrating viruses which infect dividing cells. The retrovirus genome includes two LTRs, an encapsidation sequence and three coding regions (gag, pol and env). Replication defective non-infectious retroviral vectors are manipulated to destroy the viral packaging signal, but retain the structural genes required to package the co-introduced virus engineered to contain the heterologous gene and the packaging signals. Thus, in recombinant replication defective retroviral vectors, the gag, pol and env genes are generally deleted, in whole or in part, and replaced with a heterologous nucleic acid sequence of interest. These vectors can be constructed from different types of retroviruses, such as HIV (human immuno-deficiency virus), MoMuLV (murine Moloney leukaemia virus), MSV (murine Moloney sarcoma virus), HaSV (Harvey sarcoma virus), SNV (spleen necrosis virus), RSV (Rous sarcoma virus), and Friend virus. Suitable packaging cell lines have been described in the prior art, in particular, the cell line PA317 (U.S. Pat. No. 4,861,719); the PsiCRIP cell line (PCT Publication No. WO 90/02806) and the GP+envAm-12 cell line (PCT Publication No. WO 89/07150). In addition, recombinant retroviral vectors can contain modifications within the LTRs for suppressing transcriptional activity as well as extensive encapsidation sequences which may include a part of the gag gene (Bender et al., J. Virol. 1987, 61:1639). Recombinant retroviral vectors are purified by standard techniques known to those having ordinary skill in the art.

Retrovirus vectors can also be introduced by DNA viruses, which permits one cycle of retroviral replication and amplifies tranfection efficiency (see PCT Publications No. WO 95/22617, WO 95/26411, WO 96/39036, WO 97/19182).

In a specific embodiment of the invention, lentiviral vectors can be used as agents for the direct delivery and sustained expression of a transgene in several tissue types, including brain, retina, muscle, liver, and blood. This subtype of retroviral vectors can efficiently transduce dividing and nondividing cells in these tissues, and maintain long-term expression of the gene of interest (for a review, see, Naldini, Curr. Opin. Biotechnol. 1998, 9:457-63; Zufferey, et al., J. Virol. 1998, 72:9873-80). Lentiviral packaging cell lines are available and known generally in the art (see, e.g., Kafri, et al., J. Virol., 1999, 73: 576-584).

Non-viral vectors. In another embodiment, the invention provides non-viral vectors that can be introduced in vivo, provided that these vectors contain a targeting peptide, protein, antibody, etc. that specifically binds HALR. For example, compositions of synthetic cationic lipids, which can be used to prepare liposomes for in vivo transfection of a vector carrying an anti-tumor therapeutic gene, are described in Felgner et. al., Proc. Natl. Acad. Sci. USA 1987, 84:7413-7417; Felgner and Ringold, Science 1989, 337:387-388; Mackey, et al., Proc. Natl. Acad. Sci. USA 1988, 85:8027-8031; and Ulmer et al., Science 1993, 259:1745-1748. Useful lipid compounds and compositions for transfer of nucleic acids are described, e.g., in PCT Publications No. WO 95/18863 and WO96/17823, and in U.S. Pat. No. 5,459,127. Targeting peptides, e.g., laminin or HALR-binding laminin peptides, and proteins such as anti-HALR antibodies, or non-peptide molecules can be coupled to liposomes covalently (e.g., by conjugation of the peptide to a phospholipid or cholesterol; see also Mackey et al., supra) or non-covalently (e.g., by insertion via a membrane binding domain or moiety into the bilayer membrane).

Alphavirus, Particularly, Sindbis Virus Vectors

Alphaviruses are well known in the art, and include without limitation Equine Encephalitis viruses, Semliki Forest virus and related species, Sindbis virus, and recombinant or ungrouped species (see Strauss and Strauss, Microbiol. Rev. 1994, 58:491-562, Table 1, p. 493).

Preferably, the alphaviral vectors of the invention are prepared as a replication defective virus. As used herein the term "replication defective virus" has its ordinary meaning, i.e., a virus that is propagation incompetent as a result of modifications to its genome. Thus, once such recombinant virus infects a cell, the only course it can follow is to express any viral and heterologous protein contained in its genome, and, in the case of Sindbis and other alphavirus vectors, induce apoptosis. In a specific embodiment, the replication defective alphavirus-based vectors of the invention contain genes encoding nonstructural proteins, and are self-sufficient for RNA transcription and gene expression. However, these vectors lack genes encoding structural proteins, so that a helper genome is needed to allow them to be packaged into infectious particles. In addition to providing therapeutically safe vectors, the removal of the structural proteins increases the capacity of these vectors to incorporate more than 6 kb of heterologous sequences. In another embodiment, propagation incompetence of the alphavirus vectors of the invention is achieved indirectly, e.g., by removing the packaging signal which allows the structural proteins to be packaged in virions being released from the packaging cell line.

Because Sindbis virus does not pose a significant health hazard, it can be also used in a propagation-competent form. In other words, unlike most viral vectors, it is not essential to make Sindbis virus vectors defective or replication incompetent, although this is preferred for rigorous safety reasons. Accordingly, the invention contemplates both propagation defective and propagation competent Sindbis virus vectors.

As noted above, alphaviruses, particularly Sindbis virus vectors, naturally induce apoptosis, also called "programmed cell death". Apoptosis is an intrinsic cellular process that leads to nuclear destruction, digestion of DNA, and ultimately cell necrosis and ablation. The apoptotic potential of a vector of the invention can be tested in vitro using cells in tissue culture (e.g., any of the host cells discussed in Example 1, infra).

Various methods for the preparation of alphavirus vectors of the invention are known in the art. In the case of Sindbis virus-based vectors, in general, vector preparation involves co-transfection of a packaging cell line with a capped mRNA containing Sindbis non-structural genes and, optionally, a heterologous gene under control of a Sindbis subgenomic promoter) and a helper plasmid vector that expresses Sindbis structural genes (see FIG. 1). The capped mRNA can be produced by in vitro transcription.

Various cell lines can be used as packaging cells. These include mammalian cell lines such as CHO (Chinese hamster ovary), BHK (baby hamster kidney), HuH7 (human hepatocellular carcinoma), and the like. One drawback of these cell lines is that production of Sindbis virus vectors induces apoptosis, resulting in destruction of the packaging cell within hours or a few days of co-transfection. Thus, new packaging cells must be prepared on an ongoing basis. In addition, Sindbis virus-based vectors produced in mammalian cells appear to efficiently interact with the negatively charged glucosaminoglycan heparan sulfate leading to increased viral clearence and decreased infectivity (see, e.g., Byrnes and Griffin, 2000, J. Virol., 74:644-651).

To avoid these problems, the present inventors have developed a Sindbis virus packaging cell line derived from insect cells, preferably the C6/36 mosquito cells (see co-owned, co-pending PCT Application No. PCT/US02/09431, [Attorney Internal Reference No. 5986/2H995-WO0], filed on even date herewith, entitled "Packaging Cell Lines for the Continuous Production of Alphavirus Vectors", based on U.S. Provisional Patent Application Ser. No. 60/279,048, filed Mar. 27, 2001, both of which are specifically incorporated herein by reference in its entirety). To generate the insect packaging cell line, the present inventors have stably transformed C6/36 cells with two DNA vectors, one encoding the nonstructural genes nsp 1-4 for replicating viral RNA and another (helper) encoding the structural proteins (capsid protein C, E1, E2, E3, and 6K) and the packaging signal. As unexpectedly discovered by the present inventors, these insect-derived packaging cells are substantially resistant to the apoptosis-induced properties of Sindbis vectors and can be engineered to establish long-term vector producing cultures which give rise to consistently high virus titers. In addition to C6/36 mosquito cells, non-limiting examples of other insect cell lines for use in the present invention include u4.4 cells, High Five™ cells, Schneider's *Drosophila* cell line 2, *Spodoptera frugiperda* SF9 cells, and C7-10 cells.

In each case, alphavirus, particularly Sindbis virus, particles containing the replication defective viral genome can be harvested from the packaging cell culture supernatants, concentrated and purified by any of the techniques known in the art. These techniques include, but are not limited to, centrifugation and ultracentrifugation; chromatography on ion exchange, size exclusion, hydrophobic interaction, hydrophilic interaction, or other types of columns; filtration and ultrafiltration; affinity purification; or various other techniques known in the art. Isolated viral particles of the invention can be either preserved in a solution or, preferably, lyophilized and preserved in a form of a powder.

Anti-tumor Therapeutic Genes

The therapeutic vectors of the invention can carry an anti-tumor therapeutic gene, as disclosed herein. In particular, because alphavirus, particularly Sindbis virus, vectors of the invention can carry a therapeutic gene payload, they may be modified to include any of the gene therapies described below.

The term "anti-tumor gene therapy" as used herein refers to a gene therapy targeted to a tumor, which causes tumor necrosis, apoptosis, growth regulation, i.e., regression or suppression of the tumor. Examples of anti-tumor gene therapies include, but are by no means limited to, introduction of a suicide gene, introduction of an apoptosis gene, introduction of a tumor suppressor gene, and introduction of an oncogene antagonist gene. Preferably anti-tumor genes are supplemented with immunostimulatory genes to enhance recruitment and activation of immune effector cells, including mobilized dendritic cells, to the tumor.

Thus, "gene therapy" specifically refers to transfer of a gene encoding an effector molecule into cells, in this case, into tumor cells.

Suicide gene therapies. Introduction of genes that encode enzymes capable of conferring to tumor cells sensitivity to chemotherapeutic agents (suicide gene) has proven to be an effective anti-tumor gene therapy. The present invention provides a method of treating cancer in part by introducing a gene vector, encoding a protein capable of enzymatically converting a prodrug, i.e., a non-toxic compound, into a toxic compound. In the method of the present invention, the therapeutic nucleic acid sequence is a nucleic acid coding for a product, wherein the product causes cell death by itself or in the presence of other drugs. A representative example of such a therapeutic nucleic acid is one which codes for thymidine kinase of herpes simplex virus (HSV-tk). Additional examples are thymidine kinase of varicella zoster virus (VZV-tk) and the bacterial gene cytosine deaminase.

The prodrug useful in the methods of the present invention is any that can be converted to a toxic product, i.e., toxic to tumor cells. Representative examples of such a prodrug is ganciclovir, which is converted in vivo to a toxic compound by HSV-tk (Chen et. al., Cancer Res. 1996, 56: 3758-3762). Other representative examples of prodrugs include acyclovir, FIAU [1-(2-deoxy-2-fluoro-β-D-arabinofuranosyl)-5-iodouracil], 6-methoxypurine arabinoside (converted by VZV-tk), and 5-fluorocytosine (converted by cytosine deaminase).

Prodrugs, may be readily administered to a patient by a physician having ordinary skill in the art. Using methods known in the field, such physician would also be able to determine the most appropriate dose and route for the administration of the prodrug. For example, ganciclovir is preferably administered in a dose of from about 1-20 mg/day/kg body weight; acyclovir is administered in a dose of from about 1-100 mg/day/kg body weight, and FIAU is administered in a dose of from about 1-50 mg/day/kg body weight.

Apoptosis-inducing, Anti-oncogene, and Tumor Suppressor Gene Therapies.

Tumor initiation and progression in many cancer types are linked to mutations in oncogenes (e.g., ras, myc) and tumor suppressor genes (e.g., Rb, p53). A number of approaches are being pursued using anti-oncogene and/or tumor suppressor effector molecules including monoclonal and single chain antibodies, antisense oligonucleotides, ribozymes, analogs, and immunogenic peptides (Chen, Mol. Med. Today 1997, 3:160-167; Spitz, et al., Anticancer Res. 1996, 16:3415-3422; Indolfi et al., Nat. Med. 1996, 2:634-635; Kijima et al., Pharmacol. Ther. 1995, 68:247-267; PCT Publications No. WO 94/24297 and WO 97/16547; French Patent Application No. FR 08729). These molecules specifically suppress tumor growth and increase the apoptosis rate in tumor cells. Their mechanisms of action require constant presence of suppressor or anti-oncogene molecules for sustained responses, however, they have not been shown to induce tumor-specific immunity, which has the potential of memory necessary for protection against the recurrence of the disease. Combination of these tumor growth-specific strategies with immunostimulatory therapies will have a synergistic effects on tumor regression and induction of protective immune response.

Immunostimulatory therapies. The invention also provides for immune cell stimulation, such as dendritic cell (DC) mobilization, to generate a strong anti-tumor immune response. The term "dendritic cell (DC) mobilizing agent" refers to a molecule that activates DC functional activity. A well-known DC mobilizing agent is flt-3 ligand (flt-3L). Anti-tumor-based immunotherapy efficacy can be enhanced by the addition of a variety of cytokines. Cytokines such as IL-12 amplify the antigen presenting and immunomodulatory capabilities of DC and inhibit tumor angiogenesis, which consecutively can induce immune susceptibility of the tumor. Conversely, cytokines such as IL-7 may induce more potent T cell responses and effectively reverse T cell defects in vivo. As disclosed herein, other cytokines, such as granuclocyte-macrophage colony stimulating factor (GM-CSF), IL-2, IL-3, IL-4, TNF-α, and c-kit ligand can be also used in combination with the DC mobilizing agent.

These cytokines can be administered, e.g., as soluble or microparticle encapsulated protein or by introducing the gene in viral or non-viral vectors including the vectors of the present invention. Systemic delivery of such cytokines along with local anti-tumor gene therapies may increase the tumor distribution of these cytokines, which may be required for long term reversal of T cell defects and effective tumor responses. These cytokines, depending on the mode of administration, may have a critical role in exploiting the immune inflammation for an efficient anti-tumor immune response.

Tumor growth inhibitors. The term "tumor growth inhibitor" is used herein to refer to a protein that inhibits tumor growth, such as but not limited to interferon (IFN)-γ, tumor necrosis factor (TNF)-α, TNF-β, and similar cytokines. Alternatively, a tumor growth inhibitor can be an antagonist of a tumor growth factor. Such antagonists include, but are not limited to, antagonists of tumor growth factor (TGF)-β and IL-10. The present invention contemplates administration of tumor growth inhibitor proteins systemically, or alternatively by gene therapy.

Anti-angiogenic factors. Tumor angiogenesis is an integral part of tumor progression and a variety of therapies targeted to inhibit angiogenesis are under development as cancer therapies. Anti-angiogenesis therapies primarily reverse the growth/apoptosis balance of the tumor and induce dormancy. Once the administration of these therapies is halted, angiogenesis can resume and tumor growth progresses. Anti-angiogenesis is a powerful mechanism to specifically reduce the bulk of the tumor without adverse side effects in patients. The dormancy therapy induced by anti-angiogenesis paves the way for other therapy schemes to succeed by debulking the tumor, altering the tumor microenvironment, eliminating the immunosuppressive effects, and making the tumor more susceptible for immune-mediated clearance.

An "anti-angiogenic factor" is a molecule that inhibits angiogenesis, particularly by blocking endothelial cell migration. Such factors include without limitation fragments of angiogenic proteins that are inhibitory (such as the amino terminal fragment of urokinase [PCT Publication No. WO 93/15199]); angiostatin (O'Reilly et al., Cell 1994, 79:315-328); endostatin; soluble forms of receptors for angiogenic factors, such as urokinase receptor or FGF/VEGF receptor (Wilhem et al., FEBS Letters 1994, 337:131-134); molecules which block endothelial cell growth factor receptors (O'Reilly et. al. Cell 1997, 88:277-285; O'Reilly, Nat. Med. 1996, 2:689-692), and Tie-1 or Tie-2 inhibitors. The present invention contemplates administration of anti-angiogenesis factors systemically, or alternatively by gene therapy. Preferably, an anti-angiogenic factor for use in the invention is a protein or polypeptide, which is encoded by a gene contained in the vectors of the invention.

Vector Therapy

As noted above, the alphavirus-based vectors, and particularly Sindbis virus-based vectors, of the invention can be used to treat various cancers. Also, the non-alphavirus-based vectors of the invention can be used to treat any cancer in which tumor cells express increased levels of HALR.

Isolated, preferably purified viral vector obtained as described above can be formulated in a pharmaceutical composition for administration to a patient. As used herein, a "pharmaceutical composition" includes the active agent, i.e., the viral vector, and a pharmaceutically acceptable carrier, excipient, or diluent. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

For human therapy, the viral vectors will be prepared in accordance with good manufacturing process (GMP) standards, as set by the Food & Drug Administration (FDA). Quality assurance (QA) and quality control (QC) standards will include testing for replication competent virus (if the virus vector is replication defective), activity (colony forming units [CFU] per number of viral particles, tested by induction of apoptosis or cytopathic effect (CPE), or by expression of a marker gene such as β-galactosidase), toxicity, and other standard measures.

In order to treat the tumor cells, the pharmaceutical composition is administered by any route that will permit homing of the vector to the tumor cells. Preferably, administration is parenteral, including, but not limited to, intravenous, intraarteriole, intramuscular, intradermal, subcutaneous, intraperitoneal, intraventricular, and intracranial administration. As disclosed herein, viral vectors can be also administered to the tumor-bearing animal via intranasal or oral route (see Hardy, In: *The Arbiviruses: Epidemiology and Ecology*, Ch. 4, pp. 87-126). Importantly, however, in contrast to other viral vectors in gene therapy, administration of alphavirus and non-alphavirus HALR-targeted vectors of the invention need not be locally to the tumor. Indeed, one of the advantages of this invention is the high specificity and affinity of the vector for cancer cells, even micrometastases that cannot be resected or located by standard techniques (e.g., CAT scanning, MRI scanning, etc.).

In therapeutic treatments of the invention, a therapeutically effective amount of the vector is administered to a patient. As used herein, the term "therapeutically effective amount" means an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host. Specifically, a therapeutically effective amount will cause one or more of the following: apoptosis of tumor cells; necrosis of tumor cells; elimination or prevention of tumor metastases; reduction in the rate of tumor growth; reduction in tumor size or tumor shrinkage; scab formation over cutaneous tumor; elimination of the tumor; remission of the cancer; an increase in the time for reappearance of the cancer; and increased time of survival of the patient. The frequency and dosage of the vector therapy can be titrated by the ordinary physician using standard dose-to-response techniques, but generally will be in the range of from $10^6$ to $10^{12}$ viral particles per dose administered daily, weekly, biweekly, or monthly at least twice and preferably at least three times.

Combination Therapies

Vaccines. In order to increase the tumor antigen specific immune response, one could introduce defined tumor-associated antigens (TAA) in the system to specifically increase the level of antigen. These TAA could be introduced, e.g., as proteins, peptides or as heterologous genes encoded by the viral vectors of the invention. Immunization with these antigens could either follow or occur during DC mobilization and anti-tumor gene therapy schemes. Essentially, this strategy enhances an effective immune response against specific antigen in conjunction with overall immune response. Specific immunization may lead to the expression of an immune enhancing cytokine milieu which can promote the response against the antigens released by the tumor necrosis. Such immunization could be combined with immune activating cytokines (protein or genes) to further enhance the effects.

Besides the defined antigen-based vaccines, a number of vaccine strategies are being explored in the laboratory as well as in the clinic. One well researched strategy in animal models is the modification of autologous or allogeneic tumor cell using cytokine genes (e.g., IL-2, GM-CSF, IL-12, IL-4) as well as some key costimulatory molecule genes (e.g., B7.1, B7.2). These gene modified tumor vaccines prove the concept of breaking peripheral tolerance and anergy using immunological mechanisms (Clary et al. Cancer Gene Ther. 1997, 4:97-104; Gilboa, Semin. Oncol. 1996, 23:101-107). Other similar approaches include use of tumor lysates, proteins, or RNA pulsed DC and fusion of tumor cells with DC to induce a potent tumor immune response. All these approaches have a common theme, which is the delivery of antigenic molecules to the DC to induce efficient processing and presentation of these antigens to T cells. Since these schemes are based on the availability of DC, DC mobilization is expected to amplify the effects observed with these approaches.

Chemotherapeutic agents, radiation, and surgery (tumor resection). Although the methods of the invention are effective in inhibiting tumor growth and metastasis, the vectors and methods of the present invention are advantageously used in conjunction with other treatment modalities, including without limitation surgery, radiation, chemotherapy, and other gene therapies. For example, the vectors of the invention can be administered in combination with nitric oxide inhibitors, which have vasoconstrictive activity and reduce blood flow to the tumor. In another embodiment, a vector of the invention can be administered with a chemotherapeutic such as, though not limited to, taxol, taxotere and other taxoids (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publications No. WO 91/17976, WO 93/00928, WO 93/00929, and WO 96/01815), or other chemotherapeutics, such as cis-platin (and other platin intercalating compounds), etoposide and etoposide phosphate, bleomycin, mitomycin C, CCNU, doxorubicin, daunorubicin, idarubicin, ifosfamide, and the like.

EXAMPLES

The following examples illustrate the invention without limiting its scope.

Example 1

Sindbis Vectors Mediate Potent Anti-Tumor Activity

Materials and Methods

Cell lines. Babyhamsterkidney (BHK-21, ATCC Accession No. CCL-10) and ovarian carcinoma (ES-2, ATCC Accession No. CRL-1978) cells were obtained from the American Type Culture Collection (ATCC, Manassas, Va.) and maintained in minimum essential α-modified media (αMEM, JRH Bioscience, Lenexa, Kans.) supplemented with 5% fetal bovine serum (FBS, Gemini Bioproducts, Inc., Calabasas, Calif.). A human hepatocellular carcinoma cell line HuH7 was obtained from Dr. H. Yamamoto (Hyogo College of Medicine, Japan) and maintained in Dulbecco's modified Eagle's medium (DMEM, JRH Bioscience, Lenexa, Kans.) supplemented with 10% FBS. HT29 human colorectal adenocarcinoma cells (ATCC Accession No. HTB-38) were obtained from the ATCC and maintained in McCoy's 5A medium (Iwakata & Grace modification, Mediatech, Inc, Herndon, Va.) with 10% FBS. CFPAC-1 pancreatic cancer cells (ATCC Accession No. CRL-1918), SKOV-3 ovarian adenocarcinoma cells (ATCC Accession No. HTB-77), and A431 epidermoid carcinoma cells (ATCC Accession No. CRL-2592) were obtained from the ATCC and maintained in DMEM/low modified (JRH Bioscience, Lenexa, Kans.) with 10% FBS. A498 renal cancer cells (ATCC Accession No. HTB-44), HT1197 bladder cancer cells (ATCC Accession No. CRL-1473), and LS174T colon carcinoma cells (ATCC Accession No. CL-188) were obtained from the ATCC and were maintained in minimum essential medium Eagle with Earle's salts and L-glutamine (Mediatech Inc., Herndon, Va.) supplemented with 10% FBS. All basal media above were supplemented with 100 mg/mL of penicillin-streptomycin (Mediatech, Inc., Herndon, Va.) and 0.5 mg/ml of Amphotericin B (Mediatech, Inc., Herndon, Va.).

Vectors. FIG. 1 shows schematic representation of the Sindbis virus-derived expression and helper vectors (see also Bredenbeek et al., J. Virol., 1993, 67:6439-6446, Invitrogen Co., Carlsbad, Calif.). A Sindbis virus-based expression vector SinRep/LacZ encodes the viral packaging signal, non-structural proteins nsp1-4 essential for replicating the RNA transcript, the viral promoter for subgenomic transcription, and the LacZ reporter gene. A helper plasmid DH-BB encodes the Sindbis structural genes, i.e., capsid (C), E3, E2, 6K, and E1, which are necessary for viral packaging. Not shown in FIG. 1 are the two other Sindbis virus-based expression vectors used in the present Example, SinRep/Luc and SinRep/IL12. To construct the SinRep/Luc vector, a DNA fragment containing the firefly luciferase gene (Luc) was excised from the Nhe I site and Xba I site of the pGL3 plasmid (Promega Co., Madison, Wis.) and subcloned into the Xba I site of SinRep vector (Invitrogen Co., Carlsbad, Calif.). To construct the SinRep/IL12 vector, a Sindbis vector containing two subgenomic promoters (SinRep/2P$_{SG}$) was first constructed by the insertion of a second subgenomic promoter DNA into the multiple cloning site (MCS) downstream of the original subgenomic promoter. The deoxyoligonucleotide containing the P$_{SG}$ sequence 5'-CGCGTAAA GCATCTC-TACGGTGGTCCTAATAGTGCATG-3' (SEQ ID NO: 1) was annealed to its complementary sequence 5'-CACTATT-AGGACCACCGTCGAGATGCTTTA-3' (SEQ ID NO: 2) before ligation to the SinRep plasmid digested with Mlu I and Sph I. The murine IL12 α-subunit gene (mP35, ATCC Accession No. 87596) and the IL12 β-subunit gene (mP40, ATCC Accession No. 87595) were subcloned into the Mlu I site and the Stu I site (downstream of the Sph I site) of SinRep/2P$_{SG}$, respectively, and the final construct was named SinRep/IL12.

In vitro transcription and transfection for Sindbis virus production. Plasmids for in vitro transcription were prepared with the QIAGEN plasmid kit (QIAGEN, Chatsworth, Calif.). Plasmids DH-BB, SinRep/LacZ, and SinRep/IL12 were linearized using XhoI restriction enzyme. Plasmid SinRep/Luc was linerized using Not I restriction enzyme, since the Luc gene contains an internal Xho I site. Linearized plasmids were further purified by phenol/chloroform extraction followed by ethanol precipitation. In vitro transcription reactions, from the SP6 promoter, were carried out by using the InvitroScript Cap Kit (Invitrogen Co., Carlsbad, Calif.) or mMESSAGE mMACHINE™ high yield capped RNA transcription kit (Ambion Inc., Austin, Tex.) to produce large quantities of capped mRNA transcripts. The quality of mRNA was checked on 1% agarose gels. For co-transfection of helper DH-BB and either SinRep/LacZ, SinRep/Luc, or SinRep/IL12 into BHK cells, electroporations were performed as described before (Ohno et al., Nature Biotechnol., 1997, 15: 763-767). Electroporated cells were transferred into 10 ml of αMEM containing 5% FBS and incubated for 12 hr. Cells were then washed with phosphate-buffered saline (PBS) and incubated in 10 ml of Opti-MEM I medium (GIBCO-BRL) without FBS. After 24 hr, culture supernatants were harvested and aliquots were stored at −80° C.

Infection Assay and virus quantification. Viral supernatant dilutions (300 ml) were added to 2×10$^5$ cells in 12-well plates. After 1 hr incubation at room temperature, cells were washed with PBS and incubated with medium for 24 hrs. Viral infection was evaluated by X-gal staining: infected cells were fixed in PBS containing 0.5% glutaraldehyde for 20 min followed by washing with PBS three times; cells were then stained with PBS containing 1 mg/ml X-gal (5-Bromo-4-chloro-β-D-galactropyranoside, Fisher Scientific), 5 mM potassium ferricyanide, 5 mM potassium ferrocyanide, and 1 mM MgSO$_4$ at 37° C. for 3 hrs. Viral titers were expressed as LacZ colony forming units (CFU) per milliliter. CFU was defined in terms of cells staining blue by X-gal. For SinRep/IL12 vectors, the relative CFU was determined by RT-PCR with a primer pair specific to Sindbis genomic RNA: 5'-AGCTTCCCG-CAATTTGAGGT-3' (SEQ ID NO: 3), 5'-ACGCATGGG GCAGACACAAT-3'(SEQ ID NO: 4). Viral RNA was purified from 300 ml of Opti-MEM media containing either SinRep/LacZ (control) or SinRep/IL12 vector with 1 ml of TRIzol™ reagent (GIBCO BRL). After ethanol precipitation, all RNA samples were resuspended in 50 ml of RNase-free water. RT-PCR was performed using the Platinum™ quantitative RT-PCR ThermoScrip™ one-step system (GIBCO BRL). Relative CFUs were obtained by comparing the RT-PCR band intensities of serial dilutions of SinRep/LacZ RNA and SinRep/IL12 RNA. The RT-PCR results were then correlated with the results of X-gal staining assay for SinRep/LacZ. The titers of SinRep/Luc vectors were assayed on 12-well plates by infection of BHK cells with serial dilutions of 300 ml virus-containing Opti-MEM. After overnight incubation, the luciferase activities in cell lysates from each sample were determined using a LUMI-ONE portable luminometer (Bioscan, Inc., Washington, D.C.) for a 30 sec period.

In vitro assays of Sindbis infectivity. To estimate the infectivities of Sindbis virus against hamster and human cells, 300 ml of SinRep/LacZ or SinRep/Luc virus were incubated with 2×10$^5$ of BHK, HuH7, LS174T, ES-2, HT29, CFPAC-1, PC-3, HuH7, SKOV-3, A498, HT1197, or A431 cells cultured in 12-well plates at MOI of about 100. The next day, cells were assayed by X-gal staining or the Steady-Glo™ luciferase assay system (Promega Co.). In the Steady-Glo™ luciferase assay, the cells were aspirated and 200 ml of the basal media and 200 ml of the Steady-Glo™ reagent were added. Cells were incubated with gentle rocking for 5 min until they became detached from the plates. The cell lysates were then transfered to 12×47 mm$^2$ cuvettes (PharMingen Co.) and the luciferase activity of each was determined using a LUMI-ONE portable luminometer (Bioscan, Inc., Washington, D.C.) for a 30 sec period. For each cell line, 2 to 4 independent experiments were performed.

Cell viability assay after Sindbis infection. On day 0, 300 ml of medium containing about 10$^7$ SinRep/LacZ vector was added to each of 2×10$^5$ BHK, CFPAC-1, ES-2, HT29, LS174T, or SKOV-3 cells cultured in 12-well plates for one hour. The plates were washed with PBS, refreshed with 1 ml basal medium and incubated. On the designated day (day 0, 1, 2, 3, 4), cell culture media were collected, and the cells remaining on plates were trypsinized with 200 ml 1X trypsin EDTA (Mediatech, Inc.). Cells obtained both from the media and the plates were combined and were centrifuged for 5 min at 600 rcf (relative centrifugal force). Cell pellets were resuspended in 100 ml PBS and 10 ml of the cell suspension transferred to 90 ml trypan blue solution (Mediatech Inc.). 10 ml of the trypan blue cell mixture were counted by hematocytometry and the viability (%) was determined using formula: clear cells/(clear cells+blue cells)×100%.

Animal models and in vivo transfection. All severe combined immunodeficient (SCID) mice (C.B-17-SCID or C.B-17-SCID/bg) used were obtained from Taconic (Germantown, N.Y.) and were 6-8 weeks old at the time the experiments were begun. BHK and ES-2 cells were grown as subcutaneous tumors from an initial inoculom of $5'10^6$ cells. After approximately 10 days, the tumors reached the size of at least 1 cm$^2$ and treatment was started and designated as day 1. Tumor-bearing mice were segregated into three groups: control (n=5), SinRep/LacZ (n=5), and SinRep/IL12 (n=5). 0.5 cc of Opti-MEM containing $10^7$-$10^8$ CFU of SinRep/LacZ vector or SinRep/IL12 vector were injected intraperitoneally (i.p.) into experimental groups. The control group was left untreated or injected with PBS. The size of tumors was measured daily and calculated using the formula: (length, cm)' (width, cm)'(height, cm). SinRep/IL12 vector preparations contained high levels (10 ng/ml) mIL12 in the Opti-MEM.

For human tumor models, $4'10^6$ tumor cells such as LS174T, HT29, and CFPAC-1 were grown as subcutaneous tumors for approximately 4 weeks before treatment. Tumor-bearing mice were segregated into control (no treatment) and experimental (treated daily with 0.5 cc SinRep/LacZ containing $10^7$-$10^8$ CFU virus) groups. Tumor sizes were recorded daily using the formula (length, cm)'(width, cm)'(height, cm). The LS174T test and CFPAC-1 test had 4 mice in both control and experimental group, while HT29 test had 5 mice in both control and experimental group.

Hepatic HuH7 tumors were established by previously described methods (Kozlowski et al., Cancer Res., 1984, 44: 3522-3529). SCID mice (6 week old; Taconic, Germantown, N.Y.) were anesthetized, and a transverse incision was made in the left flank through the skin and peritoneum, exposing the spleen. Mice were injected with 2×10$^6$ HuH7 cells in 250 ml of DMEM containing 10% FBS into the portal vein through the splenic hilus using a 27.5-gauge needle (Becton Dickenson). Eight weeks after tumor injection, when tumor was palpable, mice were injected i.p. with 250 ml of Sindbis virus vector once or on three consecutive days. Control mice were injected with Opti-MEM using the same procedure. In this experiment, all mice were sacrificed the day after the final injection.

b-gal immunostaining. Immunohistochemical detection of β-galactosidase protein (β-gal) was performed on formalin-fixed paraffin embedded tissues using standard streptavidin-biotin horseradish peroxidase complex detection with 3,3-diaminobenzidine (DAB) as a chromagen and an automated immunostainer (NexES, Ventana Medical Systems, Tucson, Ariz.). Appropriate positive (cell line transfected with β-galactosidase vector) and negative controls were used. Briefly, transfected cell lines were grown under appropriate growth condition to a cell density of approximately 10$^6$ cells/ml. These cells were gently pelleted and resuspended in a small amount of media. Equal proportions of fibrin and thrombin were added to this suspension to create a fibrin/thrombin/cell clot that was fixed in 10% neutral buffered formalin. Liver/tumor samples were excised from the animals and fixed in 10% neutral buffered formalin. Both the cell clot and the tissues were fixed for 12 hrs in formalin and processed for paraffin embedding. 5 μm-thick tissue sections were prepared onto electrostatically charged glass slides and baked at 60° C. overnight. The slides were deparaffinized by three washes in xylene followed by rehydration through graded alcohols (100%, 90%, and 70%). For each sample, one slide was stained with hematoxylin and eosin while the others were used for β-gal detection by staining the cells with a anti-β-galactosidase mouse monoclonal antibody (BIODESIGN, Kennebunk, Me.), which was used at a dilution of 1:50 with overnight incubation. Cellular localization of β-gal protein was cytoplasmic.

b-gal assay. The expression of β-gal protein in tissues was investigated using the All-in-One™ b-gal assay reagent kit (PIERCE, Rockford, Ill.). The tissues were homogenized in 3 ml of PBS, with a glass Pyrex homogenizer using a type B pestle (30 strokes). Homogenized samples were centrifuged at 1000 rcf at 4° C. for 10 min. The supernatant was harvested, the pellet fraction was resuspended in 2 ml of PBS, and aliquots were harvested as tissue components. 50 ml of each aliquot were mixed with 50 ml of the b-gal assay reagent in a well of a 96-well plate. After incubation at 37° C. for 30 min, absorbance at 405 nm was read using a spectrophotometer. Each protein concentration was determined by BIORAD reagent (Bio-Rad Laboratories, Hercules, Calif.) and the results were adjusted per 100 mg of protein.

Statistical analysis of data. The in vitro infectivity data were analyzed using a standard student t test. The tumor size data, obtained from different mouse models, were analyzed with repeated-measure two-way ANOVA using GraphPad Prism version 3.0a for Macintosh (GraphPad Software, San Diego, Calif.). The significance of each factor of variation was determined by the F ratio which is equal to (Mean Square of the specific factor)/(Residual Mean square). The F ratio is present in a format: F(df of factor, df of residual) which determines the F distribution. P value is the integration of the particular F distribution from the F ratio calculated to positive infinity. For example, to determine if SinRep/LacZ caused a significant reduction of BHK tumors, the F ratio for factor SinRep/LacZ was: $F(1, 32)=5.915$, and the P value based on the $F(1, 32)$ distribution was 0.0208 which is smaller than 0.05. Therefore the effect of SinRep/LacZ on BHK tumors was considered significant. On the other hand, the effect caused by different individual subjects was not significant since the $F(32, 32)=0.3712$, and the $P=0.9968$.

The statistical interaction between two factors can be also determined by the F ratio. If the effects from both SinRep/LacZ and treatment time are additive, there is no interaction between these two factors. As disclosed below, in comparing a tumor size reduction in untreated animals with SinRep/LacZ-treated animals, the interaction between SinRep/LacZ and treatment time was significant ($F(7, 32)=5.14$, $P=0.0005$). In contrast, there was no significant interaction between virus and treatment time, when SinRep/LacZ-treated animals were compared with SinRep/IL12-treated animals ($F(14, 60)=0.8290$, $P=0.6303$), indicating similar kinetics of tumor regression.

Results

Sindbis vector infects several human tumor cell lines in vitro. Sindbis virus-based vector SinRep/LacZ (FIG. 1), which carries β-galactosidase (LacZ) gene, and SinRep/Luc, which carries the firefly luciferase (Luc) gene, efficiently infected most human tumor cell lines tested: LS174T (colon), ES-2 (ovarian), HT29 (colon), CFPAC-1 (pancreatic), PC-3 (prostate), HuH7 (liver), and SKOV-3 (ovarian). SinRep/Luc also showed low but significant infectivity of A498 (kidney) and HT1197 (bladder) cells (P<0.0001) and showed intermediate level of infectivity of A431 (epidermoid carcinoma) cells (P<0.0001). All human cell lines were infected at MOI of about 100 and the marker enzyme (β-gal) activities in cell lysates were assayed the next day as described in Materials and Methods section. Mock infections of all human cell lines above resulted in very low relative luminescence unit (RLU) readings of about 150.

Sindbis vector induces cell death upon infection of tumor cells. Sindbis virus infection of mammalian cells has been previously reported to be extremely cytotoxic due to virally-induced cell apoptosis (Levine et al., Nature, 361:739-742, 1993; Jan and Griffin, J. Virol., 73:10296-10302, 1999; Jan et al., J. Virol., 74:6425-6432, 2000; Balachandran et al., J. Virol., 74: 1513-1523, 2000). To confirm this observation for tumor cells, the present inventors tested the viability of various tumor cell lines after infection by trypan blue exclusion analysis. Following infection of six different tumor cell lines with Sindbis vector SinRep/LacZ at MOI of about 100, the rapid cell death occurred over a five-day period (day 0 to day 4). BHK cells were very sensitive to the apoptosis induced by SinRep/LacZ and the majority of them were dead by 2 days after infection. Similar results were observed with ES-2 cells. LS174T, CFPAC-1, HT29, and SKOV-3 cells required two or three additional days to achieve the same level of cell death observed with BHK cells. In control experiments, all cell lines were incubated in medium only and showed no significant cell death.

Sindbis vector shows anti-tumor effects in vivo. To evaluate the anti-tumor effects of Sindbis vectors, $5 \times 10^6$ BHK cells were inoculated subcutaneously in the lower right abdomen of severe combined immunodeficient (SCID) mice (8-10 weeks old). The choice of BHK was based on their high susceptibility to Sindbis virus infection and Sindbis-induced cell death. 10 days after inoculation, BHK tumors had usually grown to about 1 cm$^2$ in size. Mice were then separated into experimental and control groups. The experimental group received intraperitoneal (i.p.) injections of about $10^7$ SinRep/LacZ vectors carrying the b-galactosidase reporter gene or SinRep/IL12 vectors carrying two genes encoding both murine IL12 subunits (mP35 and mP40) to the left abdomen (site distant to the tumor) five times a week, while the control group mice were left untreated or were injected with PBS. All mice in the control group were sacrificed on day 12 of treatment because the tumor burden began to impair the ability to walk as well as other functions. In contrast, mice in the experimental group started to show tumor reduction on day 6 to 7 of treatment. The repeated-measure two-way analysis of variance (RM two-way ANOVA) indicates that Sindbis vectors dramatically reduced the BHK tumor size. In fact, most BHK tumor-bearing mice became tumor-free after 30 days of treatment. Although both SinRep/LacZ and SinRep/IL12 had similar kinetics of their anti-BHK tumor activity, SinRep/IL12 showed enhanced anti-tumor activity against BHK cells compared to SinRep/LacZ (P=0.0167).

Another set of mice were inoculated with $5 \times 10^6$ BHK cells and after 7 days developed tumors of about 5×5 mm$^2$. Tumor-bearing mice were segregated into control (no treatment) and experimental (daily SinRep/LacZ treatment) groups, and after three days of consecutive treatments, slides were prepared from control and experimental tumors. Hematoxylin- and eosin-stained sections revealed two distinct groups of tumors; one group of tumors had approximately 90-95% necrosis while the other group had up to approximately 30% necrosis corresponding to treated and untreated tumors, respectively. The treated tumors were smaller than the untreated tumors. Vascularity was demonstrated using immunohistochemistry for Factor VIII. These blood vessels were medium to small sized with the smaller sized blood vessels in the viable tumor areas. Necrotic tumor cells were identified as eosinophilic staining cells with loss of cellular organization and membranes. The necrotic areas in the untreated tumors were located centrally, while, in the treated tumors, the main mass was necrotic with only a rim of viable cells. Immunohistochemical b-galactosidase (b-gal) staining was obtained only in the treated animals and only in the necrotic areas. No b-gal was detected in viable tumor areas. In addition, the areas of b-gal-positive staining corresponded to the areas of Factor VIII-positive staining, demonstrating that Sindbis virus is present and delivered to the tumor by a blood-borne path. Furthermore, the distribution of necrosis and b-gal suggests that viable Sindbis virus is only present at the periphery of the treated tumors. In the treated tumors, intense and confined Tunnel-positive signals were observed along the border between viable and necrotic areas of the treated tumors. In control tumors, the apoptotic signals on the viable-necrotic border of control tumors were less intense and more diffused. Also, a larger number of sharp and clear apoptotic bodies were observed in the border regions of treated tumors. No Tunnel signal was observed in the central necrotic area of either control or treated tumors.

Injections of the SinRep/IL12 vector also resulted in enhanced reduction of BHK tumors in SCID mice (P=0.0167).

Human tumor cells LS174T (colon), HT29 (colon), and CFPAC-1 (pancreatic) were also inoculated subcutaneously and were grown to a defined size prior to treatment. SinRep/LacZ treatments were administrated to experimental groups five times a week and the control groups were left untreated or injected with PBS. As in the experiments with BHK tumors, the treatments caused significant LS174T and CFPAC-1 tumor reduction in SCID mice (P<0.0001). After about two weeks of treatment, Sindbis vector caused significant growth inhibition in LS174T and CFPAC-1 tumors and a number of tumor-free mice were also observed in response to treatment. SinRep/LacZ's anti-HT29 tumor activity was lower but still significant (P<0.0001). Based on RM two-way ANOVA analysis, all human tumor models showed no significant effects among different individual subjects.

Sindbis vector is able to target HuH7 tumors in the liver of SCID mice. The HuH7 liver tumors were induced by implantation of human hepatocellular carcinoma HuH7 cells ($2 \times 10^6$) via the portal vein through the splenic hilus. After approximately eight weeks, at which time tumor growth was evident by palpation, mice were injected i.p. (once or three times) with SinRep/LacZ vector. Tumor-bearing mice treated with SinRep/LacZ vector once or for three consecutive days were sacrificed the day after the final injection. No b-gal positive cells were found in normal liver tissue or in tumors of uninfected control sections. b-gal was also not clearly detectable in the liver tumors which were infected with Sindbis vector only once. However, it was easily detectable in the liver tumors which were infected on three consecutive days. In tumors which were injected with SinRep/LacZ three times, necrosis was also observed.

In a separate experiment, the expression of b-gal protein was quantified in various tissues after one or three treatments. As in the previous experiment, in tumor cells, there was no significant difference between mice subjected to a single infection and control mice, while mice receiving three treatments showed 12- to 18-fold higher b-gal levels than control mice in tumor cell supernatants and 19- to 38-fold higher levels in tissue samples. No significant elevation of b-gal activity was observed in liver, heart, lung, kidney, and testis, regardless of whether the animals received one or three injections of the Sindbis vector. Low but significant levels of b-gal were observed in the brains of injected mice. Despite the infectivity to brain cells, all mice treated with one or three SinRep/LacZ injections stayed healthy and showed no abnormal behavior.

NK cells enhance the anti-tumor effects of Sindbis vectors. Subcutaneous BHK tumors were induced in C.B-17-SCID mice and C.B-17-SCID/bg mice. The latter is similar to C.B-17-SCID, except that, in addition to deficiency of T and B cells, it contains the beige (bg) autosomal recessive mutation, which produces impaired chemotaxis and motility of macrophages and a deficiency in Natural Killer (NK) cells. Daily treatment with Sindbis vectors appeared to be more effective in SCID mice than in SCID/bg (P<0.0001). Thus, complete regression of tumors was obtained only in SCID mice.

Discussion

The results disclosed herein indicate that Sindbis virus-based replication defective vectors (i.e., SinRep/LacZ, SinRep/Luc, and SinRep/IL12) are capable of infecting a spectrum of human tumor cells in vitro and in vivo. As disclosed in the present Example, Sindbis vectors induce apoptosis not only in vitro in various mammalian tumor cell lines, but also, in vivo in engrafted tumors of human or rodent origin. Thus, even without the addition of any heterologous genes, Sindbis virus-based vectors can act as therapeutics against malignant tumors.

Indeed, in the present study, entry of Sindbis vectors lead to a high degree of BHK tumor apoptosis and necrosis in vivo accompanied by complete tumor regression. The treatment, which comprised multiple injections (ranging from three to over fifteen) of Sindbis vectors, did not appear to be toxic to the experimental animals, indicating that these vectors mediate almost selective infection of tumor cells. Indeed, no significant infection of heart, lung, normal liver cells, and kidney was observed. The minor brain infection, although could be detected, caused no observable clinical CNS disorder in adult (6-8 weeks old) experimental mice, which are known to be resistant to neurovirulent effects induced by Sindbis virus (Griffin, J. Infect. Dis., 133: 456-464, 1976).

As further disclosed herein, the immunostaining of BHK tumors after treatments with three injections of SinRep/LacZ demonstrated areas of extensive necrosis at the periphery of the tumor. This is in contrast to the typical necrosis seen at the center of tumors caused by hypoxia and poor nutrition, which can be readily seen in untreated mice. Furthermore, the co-localization of infectious vectors and blood vessels in the tumor demonstrates that the blood-born characteristic of Sindbis virus plays an important role in vector delivery.

The vector clearance rate in blood is another important factor, which determines the success of vector-mediated tumor targeting. Both most widely used viral vectors, retroviral vectors and adenoviral vectors, have been shown to be unstable in the bloodstream (Miyao et al., Hum. Gene Ther., 8:1575-1583, 1997; Russell et al., Hum. Gene Ther., 6:635-641, 1995; Rother et al., J. Exp. Med., 182:1345-1355, 1995; Alemany et al., J. Gen. Virol., 81:2605-2609, 2000). In contrast, blood-born alphaviruses, including Sindbis virus as well as Sindbis virus-based vectors, are stable in the bloodstream (Byrnes and Griffin, J. Virol., 74: 644-651, 2000; Bernard et al., Virology, 276: 93-103, 2000; Klimstra et al., J. Virol., 72: 7357-7366, 1998).

Despite similarities in in vitro infectivity and cytotoxicity induced by Sindbis in various cell lines, differences in anti-tumor efficacy in vivo were observed. These differences might result from different number and the permeability of blood vessels in tumor tissues, from different levels of available HALRs, and/or from the presence of additional tumor-specific receptors for the virus.

As follows from the results of the in vivo experiments disclosed herein, in addition to direct killing of tumor cells induced by Sindbis infection, the host immune system, in particular, natural killer (NK) cells, which are important for innate immunity, also contribute to the tumor elimination. Indeed, NK cells are well known for their cytotoxicity to tumors (Gumperz and Parham, Nature, 378: 245-248, 1995; Trinchieri, Adv. Immunol., 47: 187-376, 1989) and virus-infected cells (Biron et al., Annu. Rev. Immunol., 17: 189-220, 1999). It has been suggested that, when the host antiviral mechanisms become activated, signals are released, such as interferons, which lead to NK cell activation (Biron et al., 1999, supra). NK cell activation may also result from the inflammation caused by the tumor cell necrosis and the release of cell contents. IL12 has been shown to be a potent NK cell stimulatory factor, and administration of IL12 has been shown to produce potent anti-tumor and anti-metastatic activity against certain solid tumors (Biron et al., 1999, supra; Brunda et al., J. Exp. Med. 178: 1223-1230, 1993; Nastala et al., J. Immunol., 153: 1697-1706, 1994; Takeda et al., J. Immunol., 156: 3366-3373, 1996; Tsung et al., J. Immunol., 158: 3359-3365, 1997). As disclosed herein, the IL12-encoding recombinant Sindbis vector (SinRep/IL12) possesses enhanced anti-tumor cytotoxicity as compared to the Sindbis vector which does not encode IL12 (SinRep/LacZ). Since Sindbis vectors of the present invention express exogenous genes at very high levels, additional anti-tumor therapeutic genes such as tumor suppressor, cytotoxic, and cytokine genes might be ideal candidates to boost the anti-tumor efficacy of Sindbis vectors.

The use of SCID mice (which lack both B and T cells) in the in vivo experiments described above does not allow to conclusively determine whether the cytotoxic T cells and neutralizing antibodies would aid or diminish the anti-tumor activity of the Sindbis vectors of the present invention. However, even if these immune cells have a negative effect, this effect can be easily diminished. For example, previously reported successful sequential vaccinations with alphavirus-based vectors suggest that the levels of neutralizing antibody elicited after vector injection can be reduced by a proper vector design (Kamrud et al., Virology, 263: 209-219, 1999; Pushko et al., Virology, 239: 389-401, 1997; Pushko et al., Virology, 239: 389-401, 1997).

Sindbis virus-based vectors demonstrate natural targeting to tumors (probably by taking advantage of a natural differential that exists in the expression of HALRs on tumors versus normal cells). Beyond this natural advantage of Sindbis vectors, targetable Sindbis vectors recognizing cell type- or tumor-specific cell surface molecules, which retain high infectivity and titers, have been developed by the present inventors (see, e.g., Ohno et al., Nat. Biotechnol., 15: 763-767, 1997), and might allow further refinement of the in vivo targeting. The above-presented experimental data suggest that Sindbis vectors, alone or in combination with other existing treatment modalities, are useful as a new tool for cancer gene therapy.

Example 2

Use of Sindbis Vectors to Treat Human Tumors

Replication defective Sindbis virus-based vectors SinRep/LacZ and SinRep/IL12 are prepared as described in Example 1 and administered intravenously (approximately 500 μl of vector formulation containing $10^7$ CFU/ml) to patients having advanced (metastatic) melanomas, or advanced (metastatic) tumors of kidney, brain, colon, prostate, liver, pancreas, bladder, lungs, or ovaries. Treatment is performed 5 times per week for three or more weeks. The size of tumors is constantly monitored by MRI and CAT scanning, followed (when possible) by histological analysis of tumor necrosis and biopsy assays for the metastatic behavior of tumor cells.

The present invention is not to be limited in scope by the specific embodiments described herein. Indeed, various modifications of the invention in addition to those described herein will become apparent to those skilled in the art from the foregoing description and the accompanying FIGURES. Such modifications are intended to fall within the scope of the appended claims.

It is further to be understood that all base sizes or amino acid sizes, all synthetic concentrations and all molecular weight or molecular mass values, are approximate, and are provided for description.

All patents, applications, publications, test methods, literature, and other materials cited herein are hereby incorporated by reference.

What is claimed is:

1. A method for treating a mammal suffering from a tumor that expresses greater amounts of High Affinity Laminin Receptors (HALRs) than normal cells of the same lineage, which method comprises systemically administering to a mammal harboring such a tumor an amount of a replication defective Sindbis virus vector effective to target and treat the tumor, wherein the vector has not been modified to target a tumor-specific cellular determinant, has a preferential affinity for HALRs, a Sindbis virus E2 HALR binding domain, has genes encoding Sindbis proteins nsp1-4 and the vector carries a heterologous anti-tumor gene selected from the group consisting of a suicide gene, an apoptosis-including gene, a tumor suppressor gene, an oncogene antagonist gene, an immunostimulatory gene, a tumor suppressor effector gene, an antisense oligonucleotide-encoding sequence, a ribozyme-encoding sequence, and an immunogenic peptide-encoding sequence.

2. The method according to claim 1, wherein the mammal has at least a partially functional immune system.

3. The method according to claim 1, wherein the mammal is a human.

4. The method according to claim 1, wherein the tumor is a solid tumor.

5. The method according to claim 4, wherein the solid tumor is selected from the group consisting of a hepatic carcinoma, melanoma, epidermoid carcinoma, pancreatic cancer, brain malignancy, breast cancer, lung cancer, ovarian adenocarcinoma, colon cancer, prostate cancer, bladder cancer, and renal cancer.

6. The method according to claim 1, wherein said vector is administered parenterally.

7. The method of claim 1 wherein said High Affinity Laminin Receptors are unoccupied.

8. The method according to claim 1, wherein said anti-tumor gene is an apoptosis-inducing gene.

9. The method according to claim 1, wherein the anti-tumor gene is a cytokine-encoding gene.

10. The method of claim 1 wherein said suicide gene is thymidine kinase.

11. The method of claim 10 comprising administering 1-20 mg/day/kg body weight of ganciclovir to said mammal.

* * * * *

```
                          SEQUENCE LISTING

<160> NUMBER OF SEQ ID NOS: 4

<210> SEQ ID NO 1
<211> LENGTH: 38
<212> TYPE: DNA
<213> ORGANISM: artificial
<220> FEATURE:
<223> OTHER INFORMATION: subgenomic promoter

<400> SEQUENCE: 1
cgcgtaaagc atctctacgg tggtcctaat agtgcatg                          38

<210> SEQ ID NO 2
<211> LENGTH: 30
<212> TYPE: DNA
<213> ORGANISM: artificial
<220> FEATURE:
<223> OTHER INFORMATION: subgenomic promoter

<400> SEQUENCE: 2
cactattagg accaccgtcg agatgcttta                                   30

<210> SEQ ID NO 3
<211> LENGTH: 20
<212> TYPE: DNA
<213> ORGANISM: artificial
<220> FEATURE:
<223> OTHER INFORMATION: primer

<400> SEQUENCE: 3
agcttcccgc aatttgaggt                                              20

<210> SEQ ID NO 4
<211> LENGTH: 20
<212> TYPE: DNA
<213> ORGANISM: artificial
<220> FEATURE:
<223> OTHER INFORMATION: primer

<400> SEQUENCE: 4
acgcatgggg cagacacaat                                              20
```